(12) United States Patent
Yokota et al.

(10) Patent No.: US 9,731,025 B2
(45) Date of Patent: Aug. 15, 2017

(54) PHARMACEUTICAL COMPOSITION FOR TRANSCOLONIC ABSORPTION

(75) Inventors: Takanori Yokota, Tokyo (JP); Masahiro Murakami, Osaka (JP); Kazutaka Nishina, Tokyo (JP)

(73) Assignee: NATIONAL UNIVERSITY CORPORATION TOKYO MEDICAL AND DENTAL UNIVERSITY, Tokyo (JP)

( * ) Notice: Subject to any disclaimer, the term of this patent is extended or adjusted under 35 U.S.C. 154(b) by 0 days.

(21) Appl. No.: 13/817,172

(22) PCT Filed: Aug. 19, 2011

(86) PCT No.: PCT/JP2011/004642
§ 371 (c)(1),
(2), (4) Date: Apr. 26, 2013

(87) PCT Pub. No.: WO2012/023291
PCT Pub. Date: Feb. 23, 2012

(65) Prior Publication Data
US 2013/0210891 A1 Aug. 15, 2013

(30) Foreign Application Priority Data

Aug. 20, 2010 (JP) ................. 2010-185501

(51) Int. Cl.
| | | |
|---|---|---|
| *A61K 47/48* | (2006.01) | |
| *A61K 9/00* | (2006.01) | |
| *A61K 9/02* | (2006.01) | |
| *A61K 9/107* | (2006.01) | |
| *A61K 9/19* | (2006.01) | |
| *A61K 9/50* | (2006.01) | |
| *C12N 15/87* | (2006.01) | |
| *C12N 15/11* | (2006.01) | |
| *C12N 15/113* | (2010.01) | |

(52) U.S. Cl.
CPC ...... *A61K 47/48092* (2013.01); *A61K 9/0031* (2013.01); *A61K 9/02* (2013.01); *A61K 9/1075* (2013.01); *A61K 9/19* (2013.01); *A61K 9/5026* (2013.01); *A61K 9/5042* (2013.01); *A61K 47/48107* (2013.01); *C12N 15/111* (2013.01); *C12N 15/113* (2013.01); *C12N 15/87* (2013.01); *C12N 2310/11* (2013.01); *C12N 2310/12* (2013.01); *C12N 2310/14* (2013.01); *C12N 2310/16* (2013.01); *C12N 2310/3515* (2013.01); *C12N 2320/32* (2013.01)

(58) Field of Classification Search
CPC .............................................. A61K 47/48092
See application file for complete search history.

(56) References Cited

U.S. PATENT DOCUMENTS 6,395,492 B1 * 5/2002 Manoharan et al. ........ 435/6.12

FOREIGN PATENT DOCUMENTS

| | | |
|---|---|---|
| JP | 2001-261551 | 9/2001 |
| JP | 2002-510319 | 4/2002 |
| JP | 2003-524586 | 8/2003 |
| WO | WO 99/01579 | 1/1999 |
| WO | WO 99/60012 | 11/1999 |
| WO | WO 02/24161 A1 | 3/2002 |
| WO | WO 2005/042539 A1 | 5/2005 |
| WO | WO 2009/069313 A1 | 6/2009 |

OTHER PUBLICATIONS

Will et al. (Attachment of vitamin E derivatives to oligonucleotides during solid-phase synthesis Tetrahedron Letters, (May 5, 1992) vol. 33, Issue 19, pp. 2729-2732).*
Yoshikawa et al. (Biological & Pharmaceutical Bulletin. 1997; 20(10): 1116-1118).*
Attilio Rigotti (Molecular Aspects of Medicine. 2007; 28: 423-436).*
Kazuya Taniguchi, et al., "Enhanced Intestinal Permeability to Macromolecules II, Improvement of the Large Intestinal Absorption of Heparin by Lipid-Surfactant Mixed Micelles in Rat", International Journal of Pharmaceutics, vol. 4, pp. 219-228 (1980).
Shozo Muranishi, et al., Absorption of 5-Fluorouracil from Various Regions of Gastrointestinal Tract in Rat, Effect of Mixed Micelles, Pharmaceutical Society of Japan, J. Pharm. Dyn., vol. 2, pp. 286-294 (1979).
S. Muranishi, "Absorption Barriers and Absorption Promoters in the Intestine", Elsevier Science Publishers B.V. (Biomedical Division), Topics in Pharmaceutical Sciences 1987, pp. 445-455.
Masahiro Murakami, et al., "Effects of pH and Surfactant on Enhanced Intestinal Absorption Caused by Fatty Acids", Yakuzaigaro, vol. 53, No. 3, pp. 176-184 (1993).
Hiroshi Yoshikawa, et al., "Absorption of Oligodeoxynucleotide by Suppository from Rat Rectal Route", Biol. Pharma. Bull. vol. 20(10), pp. 1116-1118 (1997).
English-language International Search Report issued by the Japanese Patent Office in International Application No. PCT/JP2011/004642, mailed Sep. 20, 2011 (2 pages).

(Continued)

*Primary Examiner* — Scott Long
(74) *Attorney, Agent, or Firm* — Finnegan, Henderson, Farabow, Garrett & Dunner, LLP

(57) ABSTRACT

The present invention aims to provide a pharmaceutical composition for transcolonic absorption capable of delivering a physiologically active substance (in particular, a water-soluble physiologically active substance of high molecular weight) having an intracellular site of action into specific tissue cells with high specificity, noninvasively by a means of administration other than injection. The pharmaceutical composition for transcolonic absorption of the present invention is characterized by comprising at least the following (a) and (b);
(a) a physiologically active substance having an intracellular site of action and bound with an introduction substance into lipoprotein, and
(b) a compound having an action of enhancing large intestinal mucosal epithelial permeability of the physiologically active substance.

8 Claims, 14 Drawing Sheets

(56) References Cited

OTHER PUBLICATIONS

International Preliminary Report on Patentability issued by the International Bureau of WIPO in International Application No. PCT/JP2011/004642, mailed Aug. 7, 2012 (19 pages).
Extended European search report, for European Patent Application No. 11817940.7-1453, dated Apr. 4, 2016 (9 pgs.).

* cited by examiner

[Figure 1]
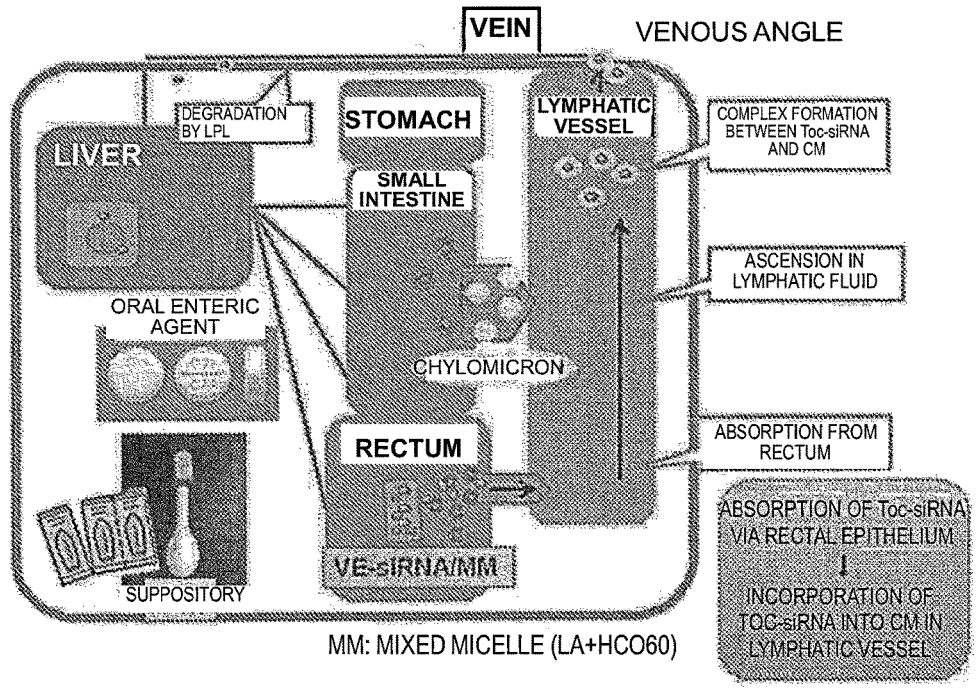

[Figure 2]
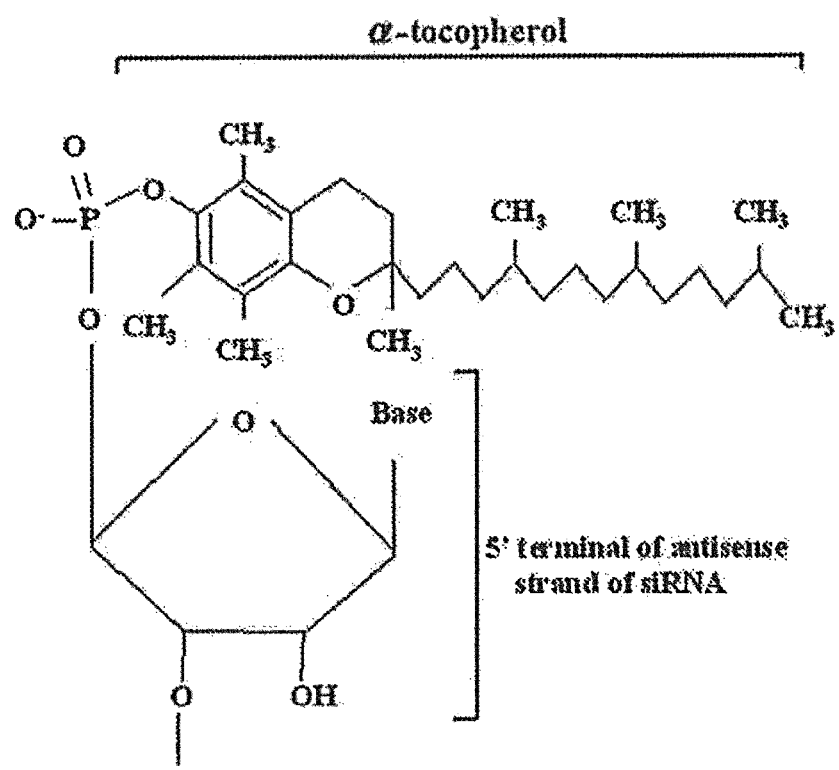

[Figure 3]
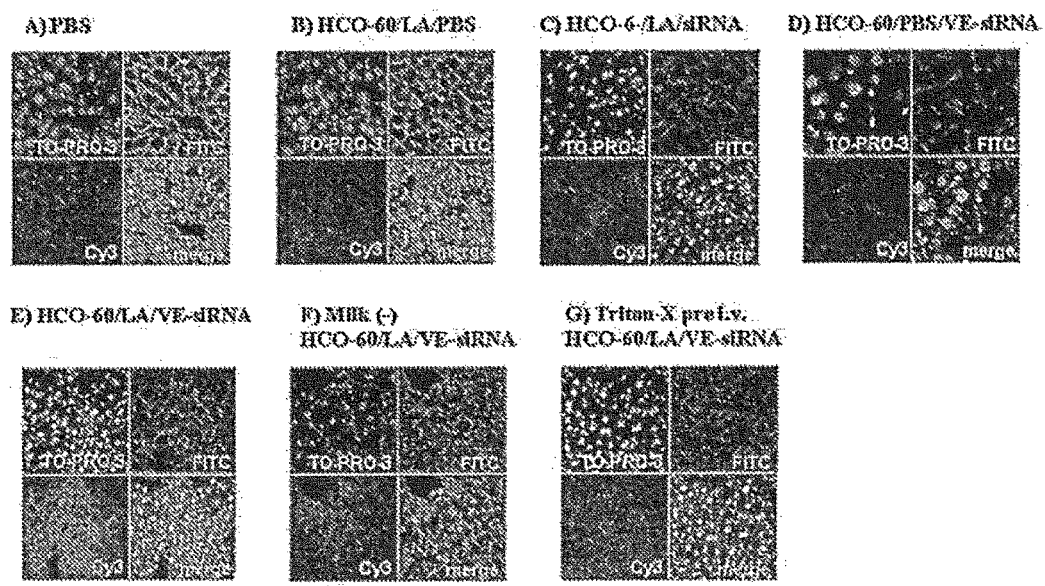

[Figure 4]
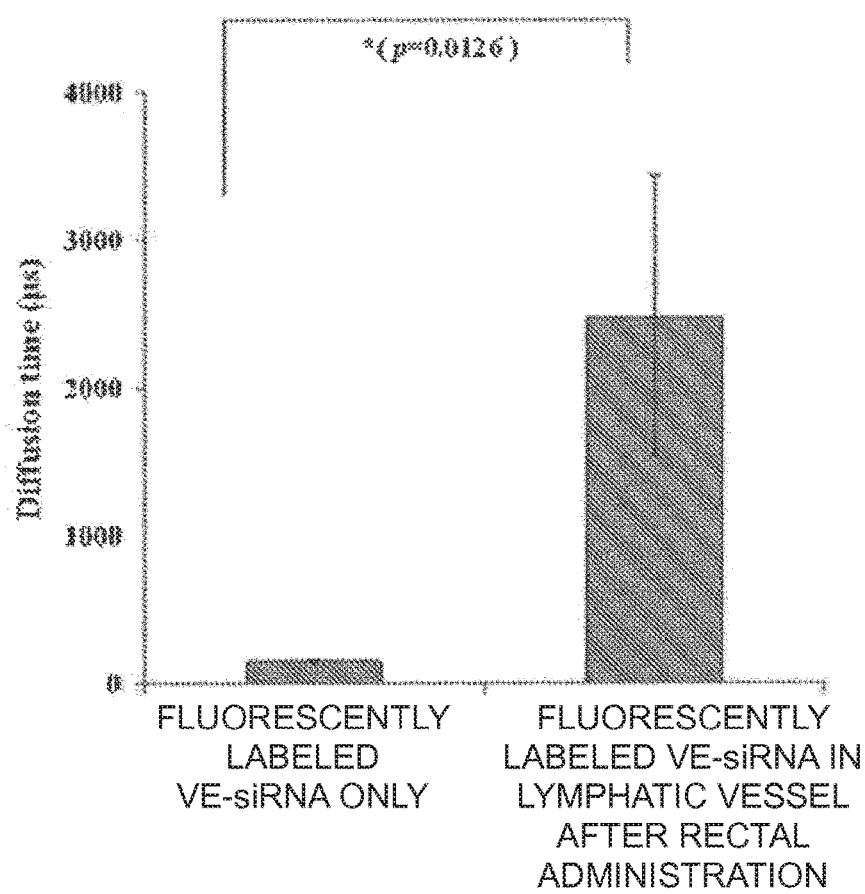

[Figure 5]
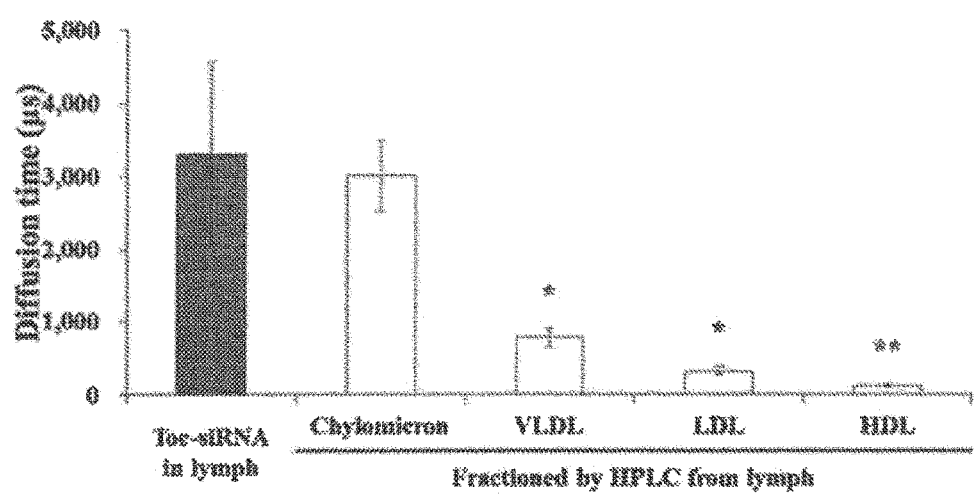

[Figure 6]
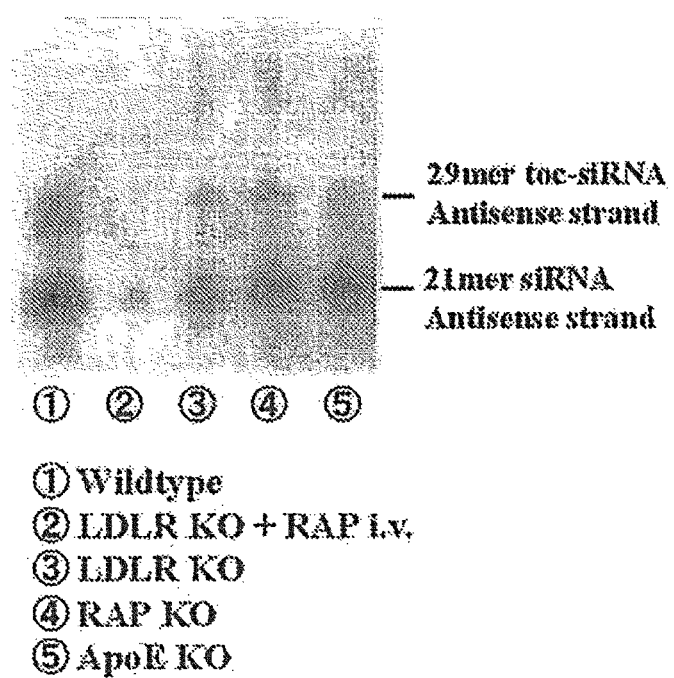

[Figure 7]
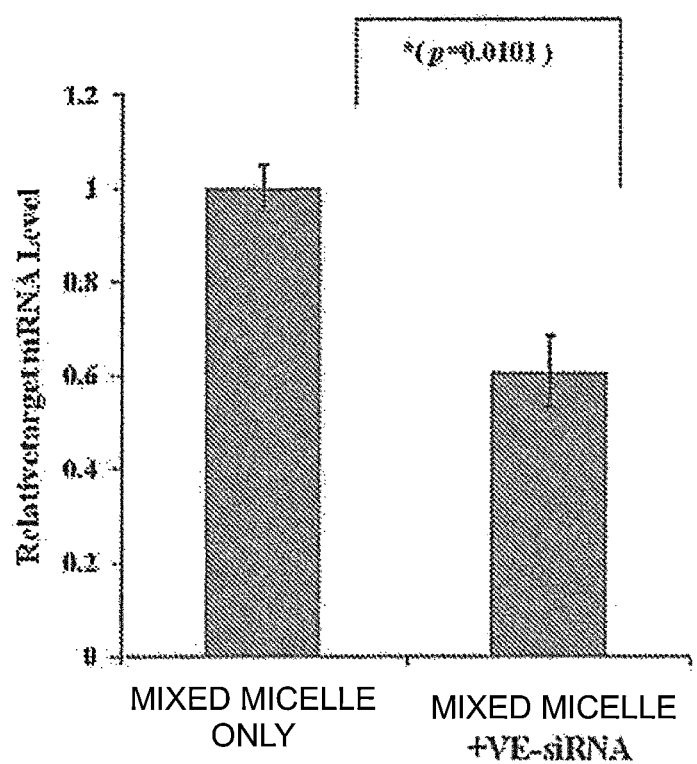

[Figure 8]
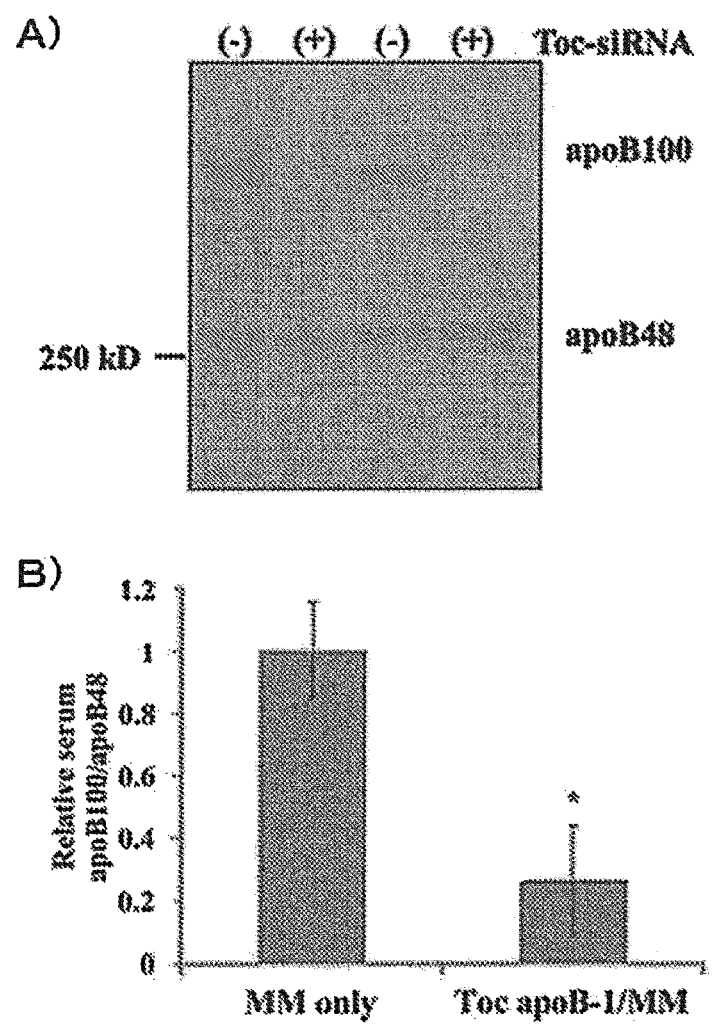

[Figure 9]
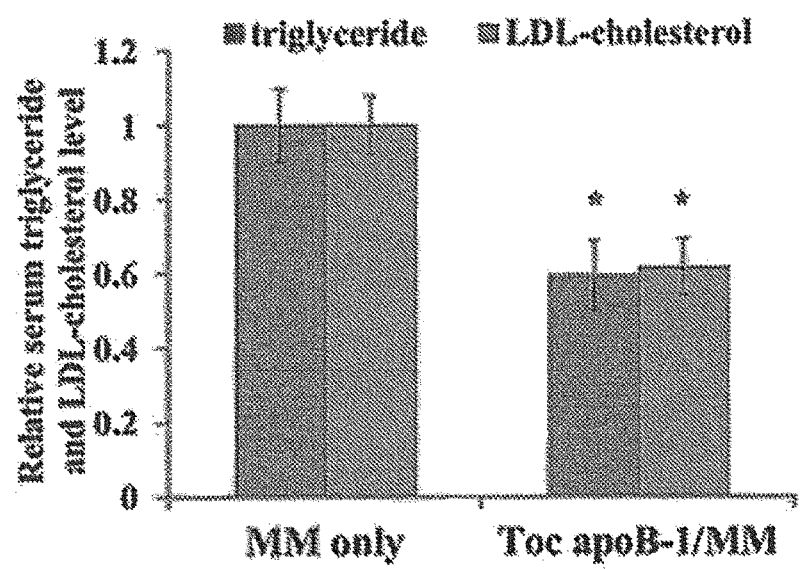
[Figure 10]
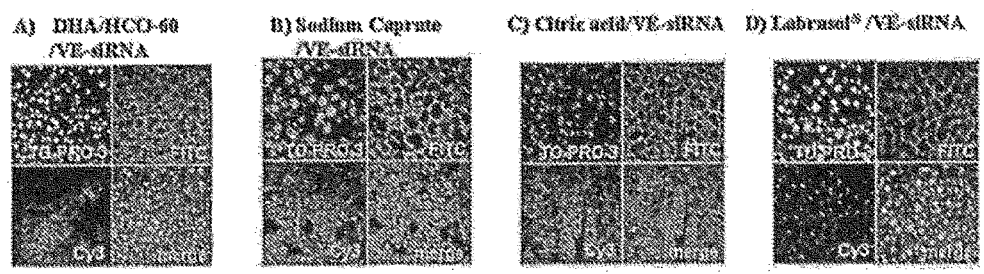

[Figure 11]
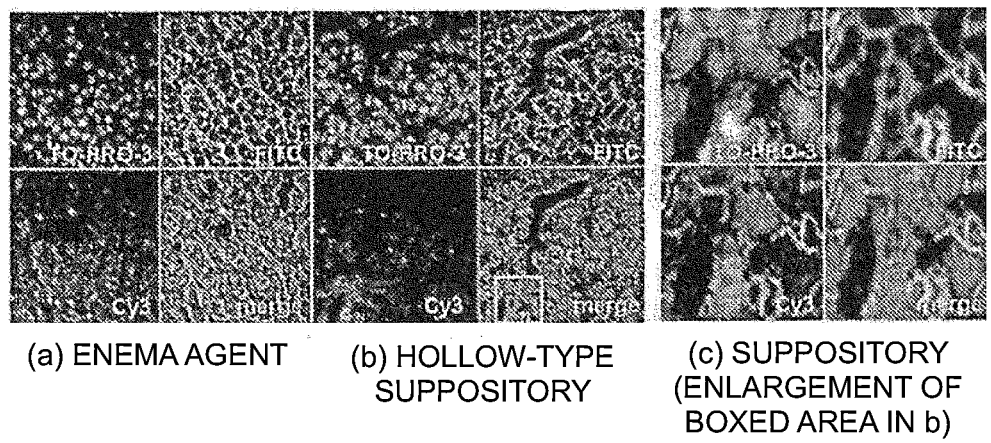
(a) ENEMA AGENT  (b) HOLLOW-TYPE SUPPOSITORY  (c) SUPPOSITORY (ENLARGEMENT OF BOXED AREA IN b)
[Figure 12]
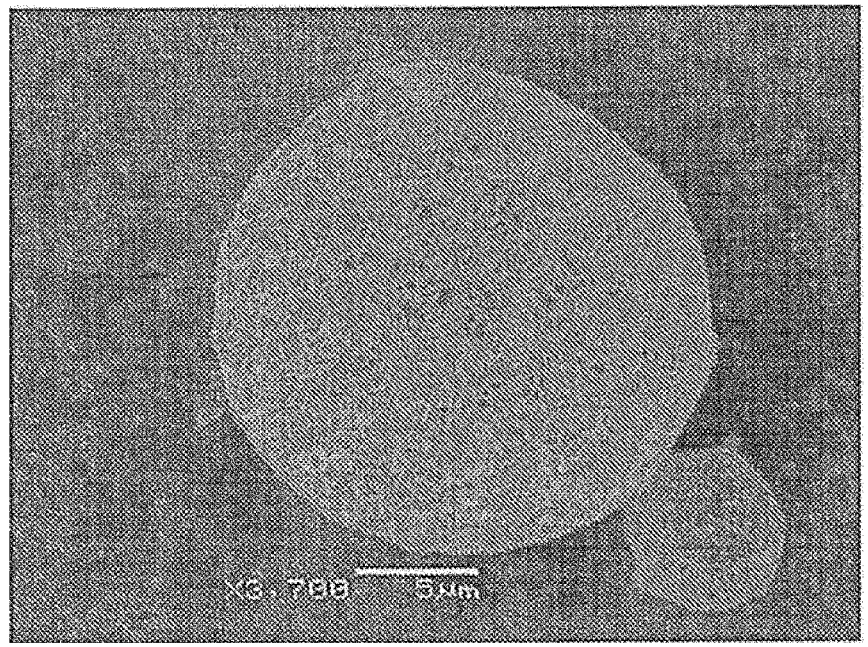

[Figure 13]
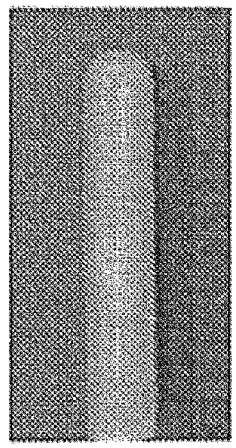

[Figure 14]
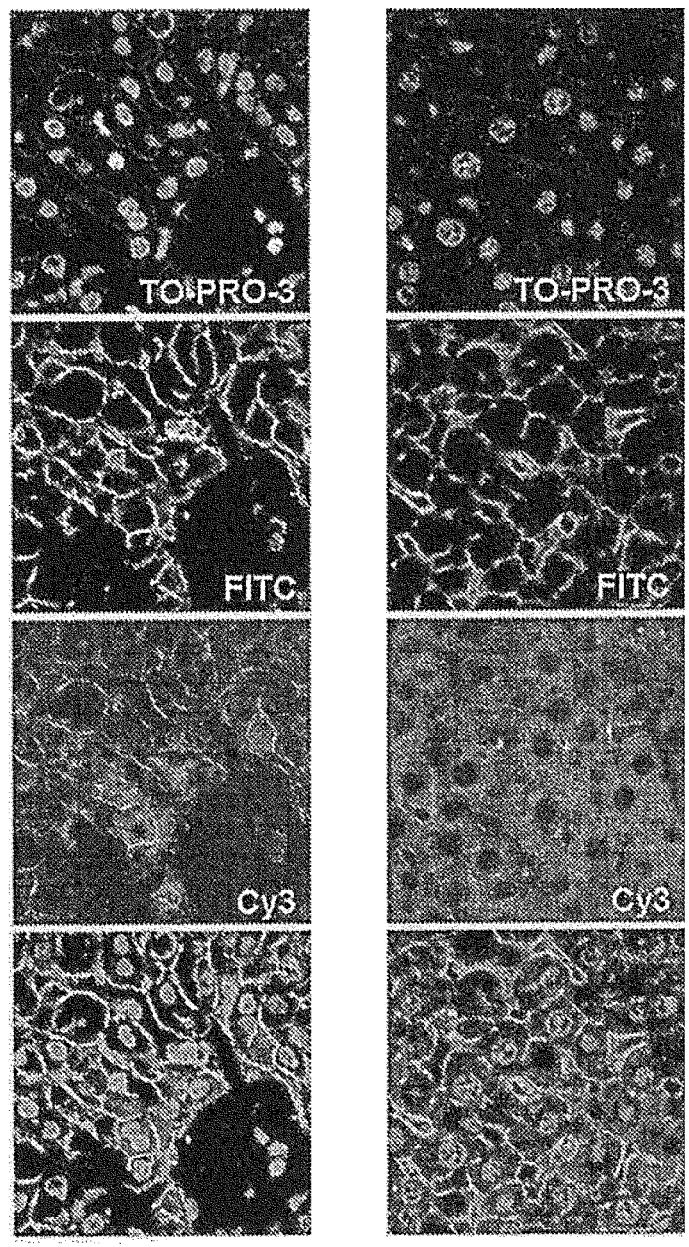
(a) p-MS ENEMA AGENT (LIVER)
(b) p-MS SUPPOSITORY (LIVER)

[Figure 15]
UPPER PART OF LARGE
INTESTINE
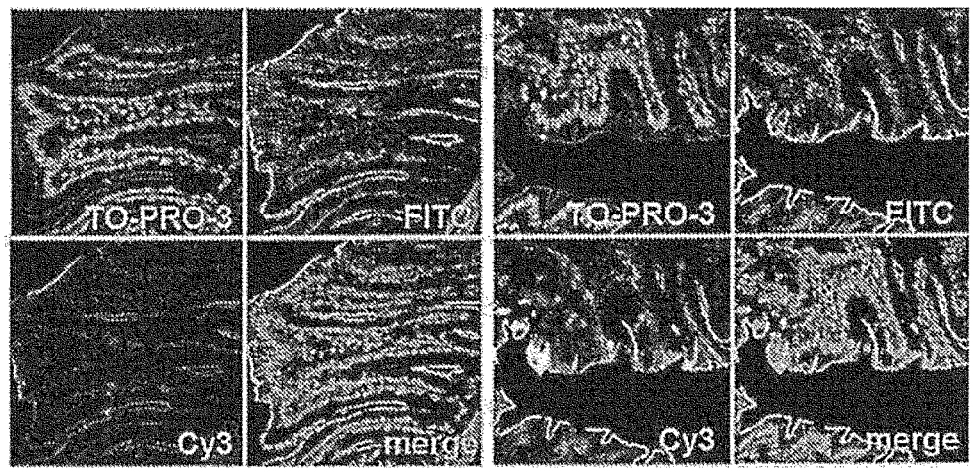
(a) p-MS ENEMA AGENT       (b) p-MS SUPPOSITORY
LOWER PART OF LARGE INTESTINE
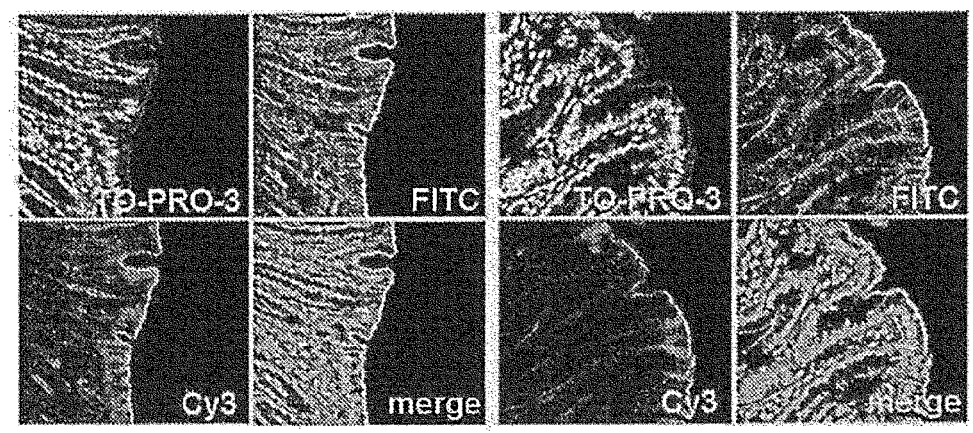
(c) p-MS ENEMA AGENT       (d) p-MS SUPPOSITORY

[Figure 16]
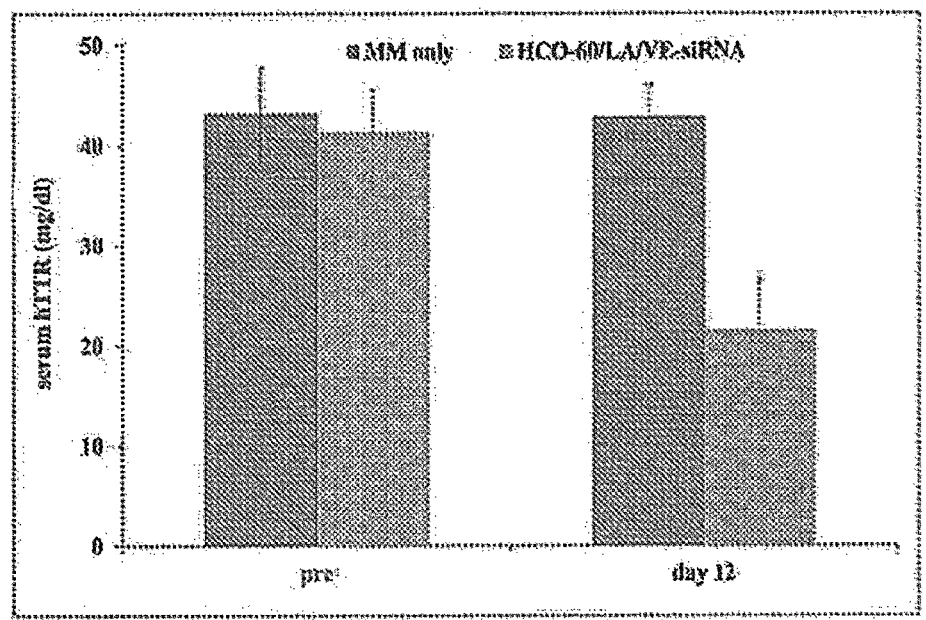

SEQUENCE LISTING

```
<160> NUMBER OF SEQ ID NOS: 4

<210> SEQ ID NO 1
<211> LENGTH: 27
<212> TYPE: RNA
<213> ORGANISM: Artificial Sequence
<220> FEATURE:
<223> OTHER INFORMATION: sense chain

<400> SEQUENCE: 1
gucaucacac ugaauaccaa ugcugga                                       27

<210> SEQ ID NO 2
<211> LENGTH: 29
<212> TYPE: RNA
<213> ORGANISM: Artificial Sequence
<220> FEATURE:
<223> OTHER INFORMATION: antisense chain

<400> SEQUENCE: 2
uccagcauug guauucagug ugaugacac                                     29

<210> SEQ ID NO 3
<211> LENGTH: 27
<212> TYPE: RNA
<213> ORGANISM: Artificial Sequence
<220> FEATURE:
<223> OTHER INFORMATION: sense chain

<400> SEQUENCE: 3
guaaccaaga guauuccauu uuuacua                                       27
```

```
<210> SEQ ID NO 4
<211> LENGTH: 29
<212> TYPE: RNA
<213> ORGANISM: Artificial Sequence
<220> FEATURE:
<223> OTHER INFORMATION: antisense chain

<400> SEQUENCE: 4
uaguaaaaau ggaauacucu ugguuacac                                              29
```

PHARMACEUTICAL COMPOSITION FOR TRANSCOLONIC ABSORPTION

TECHNICAL FIELD

The present invention relates to a pharmaceutical composition for transcolonic absorption, in more detail, to a pharmaceutical composition for transcolonic absorption comprising a specific physiologically active substance and a specific compound having an epithelial permeability-enhancing action.

BACKGROUND ART

Generally, most of the peptide pharmaceutical products such as hormones and cytokines, antibody pharmaceutical products, and nucleic acid pharmaceutical products such as siRNA and DNA plasmids are water-soluble compounds of high molecular weight. They have extremely low epithelial permeability and cell membrane permeability. Meanwhile, in many cases, the target molecule (site of action) for these physiologically active substances is present in the cell membrane or in the cells, and the development of pharmaceutical products with these physiologically active substances requires the development of a technique (system) for delivering these physiologically active substances into the target cells. Despite the fact that various drug delivery systems (DDS) have been developed until now, there is no report regarding a system for delivering these physiologically active substances specifically to the target tissues, particularly into the target cells by a means other than injection. This is deemed to be attributable to the fact that development of multifunctional DDS combining both the function of delivering drugs into the body by a means other than injection and the function of delivering drugs specifically to the target site is extremely difficult. Particularly, while the oral route is an easy drug administration route, there are many obstacles in drug delivery.

So far, the present inventors have continued their research on a system for delivering a nucleic acid for suppressing the expression of the target gene using endogenous chylomicrons, and the like. For example, Patent Document 1 describes an agent for suppressing a target gene expression, comprising nucleic acids for suppressing the target gene expression, wherein an introduction substance into chylomicron or chylomicron remnant is bound to the nucleic acids, and wherein the agent is administered to a vertebrate under a condition in which the production of an endogenous chylomicron has been induced in the vertebrate. However, the above agent for suppressing a target gene expression was supposed to be administered by injection such as intravenous injection as the main administration route.

Many of the medically important drugs are administered by injection due to poor absorption through the digestive tract. However, injection therapy imposes mental as well as physical pain on patients, and moreover, the possibility of induction of allergic reactions and tissue damage in the administration site is pointed out. In view of the foregoing, a novel dosage form alternative to an injection agent is demanded, and recently, development of orally or rectally administered agents of poorly absorbable drugs has been attempted.

For example, Non Patent Document 1 describes the possibility of utilization of, as an absorption enhancer for improving the intestinal permeability of poorly absorbable drugs, capric acid, oleic acid, linoleic acid, and their fatty acids such as monoglycerides; sugar esters of fatty acid; glycerol esters of fatty acids; chelating agents such as EDTA and citric acid; and surfactants such as sodium lauryl sulfate. Also, Non-Patent Document 2, which was written by the present inventors, describes that long-chain unsaturated fatty acid and medium-chain fatty acid are excellent absorption enhancers, and a mixed micelle of long-chain unsaturated fatty acid and HCO-60 (nonionic detergent) is particularly excellent.

PRIOR ART DOCUMENTS

Patent Documents

Patent Document 1: WO 2009/069313

Non-Patent Documents

Non Patent Document 1: D. D. Breimer and P. Speiser, Editors, "Topics in Pharmaceutical Sciences 1987", Elsevier Science Publishers B.V., Biomedical Division (1987), pp. 445 to 455.
Non Patent Document 2: Journal of Pharmaceutical Science and Technology, Japan, Vol. 53, No. 3, pp. 176 to 184 (1993)

SUMMARY OF THE INVENTION

Object to be Solved by the Invention

The present invention aims to provide a pharmaceutical composition for transcolonic absorption capable of delivering a physiologically active substance (in particular, a water-soluble physiologically active substance of high molecular weight) having an intracellular site of action into specific tissue cells with high specificity, noninvasively by a means of administration other than injection.

Means to Solve the Object

The present inventors conducted intensive studies on a method of noninvasive administration of vitamin E-conjugated siRNA (VE-siRNA) other than injection. It has been conventionally known that endogenous chylomicrons, which are one kind of lipoproteins in vivo, are formed in the small intestine, the majority of which penetrate through the mucosal epithelium of the small intestine into lymphatic vessels and ascend along the lymphatic vessels; after draining into the vein, they are metabolized into chylomicron remnants by lipoprotein lipase (LPL), whereby the endogenous chylomicron is delivered to the liver. In light of the above, the present inventors conceived of delivering endogenous chylomicrons comprising VE-siRNA into the liver cells by absorption from the small intestine by allowing formation of endogenous chylomicrons comprising VE-siRNA by administering VE-siRNA into the small intestine so as to become a constituent material of endogenous chylomicrons. In order to achieve this, they administered VE-siRNA into the small intestine in combination with various compounds having an intestinal mucosal epithelial permeability-enhancing action. However, it turned out that VE-siRNA hardly penetrated through the mucosal epithelium of the small intestine, resulting in a failure of efficient delivery of VE-siRNA into the liver cells.

In light of the above, the present inventors once thought about giving up the enteral administration of VE-siRNA. This is due to the assumption that although large intestinal administration was supposedly possible as a means of enteral administration other than small intestinal administration, due to the fact that chylomicrons are not formed in the large intestine, VE-siRNA would not be taken up by endogenous chylomicrons even with the concomitant large intestinal administration of various compounds having an intestinal mucosal epithelial permeability-enhancing action. Nevertheless, the present inventors attempted large intestinal administration of VE-siRNA in combination with various compounds having an intestinal mucosal epithelial permeability-enhancing action. As a result, they have unexpectedly found that although there is a variation in the efficiency, VE-siRNA can be efficiently delivered into the liver cells by virtue of various compounds having an intestinal mucosal epithelial permeability-enhancing action, thereby completing the present invention.

That is, the present invention relates to:
(1) a pharmaceutical composition for transcolonic absorption, comprising at least the following (a) and (b);
(a) a physiologically active substance having a site of action inside a cell and bound with an introduction substance into lipoprotein, and
(b) a compound having an action of enhancing large intestinal mucosal epithelial permeability of the physiologically active substance;
(2) the pharmaceutical composition according to the aforementioned (1), further comprising a surfactant, as the compound having an action of enhancing large intestinal mucosal epithelial permeability;
(3) the pharmaceutical composition according to the aforementioned (1) or (2), wherein the introduction substance into lipoprotein is an introduction substance into chylomicron or chylomicron remnant;
(4) the pharmaceutical composition according to the aforementioned (3), wherein the introduction substance into lipoprotein is a fat-soluble vitamin or a cholesterol;
(5) the pharmaceutical composition according to the aforementioned (4), wherein the fat-soluble vitamin is vitamin E or a derivative thereof;
(6) the pharmaceutical composition according to the aforementioned (1) or (2), wherein the pharmaceutical composition is capable of delivering the physiologically active substance specifically to a liver cell;
(7) the pharmaceutical composition according to the aforementioned (1) or (2), wherein a molecular weight of the physiologically active substance bound with an introduction substance into lipoprotein is within a range of 1000 to 150000 Da;
(8) the pharmaceutical composition according to the aforementioned (1) or (2), wherein the physiologically active substance is a nucleic acid for suppressing an expression of a target gene;
(9) the pharmaceutical composition according to the aforementioned (8), wherein the nucleic acid is one or more selected from the group consisting of siRNA, shRNA, an antisense oligonucleotide, an antagomir, a nucleic acid aptamer, a ribozyme, and a decoy;
(10) the pharmaceutical composition according to the aforementioned (1) or (2), wherein the compound having an action of enhancing large intestinal mucosal epithelial permeability comprises at least one of the following (c) and (d);
(c) a medium-chain fatty acid or a long-chain unsaturated fatty acid, and
(d) a salt, an ester, or an ether of the fatty acid according to the aforementioned (c) (including a conjugated form in a case of a polyunsaturated fatty acid);
(11) the pharmaceutical composition according to the aforementioned (10), wherein the compound having an action of enhancing large intestinal mucosal epithelial permeability is linoleic acid, oleic acid, linolenic acid, docosahexaenoic acid, eicosapentaenoic acid, capric acid, or lauric acid, or a salt, an ester, or an ether of any of the above;
(12) the pharmaceutical composition according to the aforementioned (2), wherein the surfactant is polyoxyethylene hydrogenated castor oil, polysorbate, polyethylene glycol, poloxamer, monoacylglycerol, monoacyl sorbitan, or sucrose esters of fatty acids; and
(13) the pharmaceutical composition according to the aforementioned (1) or (2), which is an agent for administration to large intestine, an oral enteric agent, or an oral drug delivery system.

Effect of the Invention

The present invention can provide a pharmaceutical composition for transcolonic absorption capable of delivering a physiologically active substance (in particular, a water-soluble physiologically active substance of high molecular weight) having an intracellular site of action into specific tissue cells with high specificity, noninvasively by a means of administration other than injection.

BRIEF DESCRIPTION OF DRAWINGS

FIG. 1 is a diagram illustrating an overview of a conceivable delivery mechanism for the pharmaceutical composition for transcolonic absorption of the present invention.

FIG. 2 is a diagram illustrating the chemical structure of VE-siRNA. In the sequence, small letters indicate 2'-O-methyl modification, asterisks indicate phosphothionate skeletons, and Toc indicates α-tocopherol.

FIG. 3 is a set of diagrams illustrating the results of confocal laser scanning microscopic observation of frozen sections prepared from the liver tissues of mice given rectal administration of substances such as fluorescently labeled VE-siRNA and an epithelial permeability-enhancing compound.

FIG. 4 is a graph illustrating the results of the analysis of the lymph fluid of mice given rectal administration of substances such as fluorescently labeled VE-siRNA and an epithelial permeability-enhancing compound by fluorescence correlation spectroscopy (FCS).

FIG. 5 is a graph illustrating the results of the analysis of the lymph fluid of mice given rectal administration of substances such as fluorescently labeled VE-siRNA and an epithelial permeability-enhancing compound, or the lipoprotein fractions of the lymph fluid by fluorescence correlation spectroscopy (FCS).

FIG. 6 is a diagram illustrating the results of the Northern blot analysis of total RNA derived from the liver cells of mice given rectal administration of substances such as VE-siRNA and an epithelial permeability-enhancing compound.

FIG. 7 is a graph illustrating the results of quantitative RT-PCR of the target endogenous gene in total RNA derived from the liver cells of mice given rectal administration of substances such as VE-siRNA and an epithelial permeability-enhancing compound.

FIG. 8 is a set of diagrams illustrating the results of the Western blot analysis of apoB100 and apoB48 in the serum of mice given rectal administration of substances such as VE-siRNA and an epithelial permeability-enhancing compound. FIG. 8 A: FIG. 8 A is a diagram illustrating the results of the Western blot assay. FIG. 8 B: FIG. 8 B is a graph illustrating the results of calculation of the ratio of the quantitative value of apoB100 to the quantitative value of apoB48 (apoB100/48 ratio) based on the quantitation of the concentration of the band from the results of FIG. 8 A.

FIG. 9 is a graph illustrating the triglyceride level and LDL-cholesterol level in the serum of mice given rectal administration of substances such as VE-siRNA and an epithelial permeability-enhancing compound.

FIG. 10 is a set of diagrams illustrating the results of confocal laser scanning microscopic observation of frozen sections prepared from the liver tissues of mice given rectal administration of substances such as fluorescently labeled VE-siRNA and a variety of epithelial permeability-enhancing compounds.

FIG. 11 is a set of diagrams illustrating the results of confocal laser scanning microscopic observation of frozen sections prepared from the liver tissues of rats given rectal administration of substances such as a hollow-type suppository comprising fluorescently labeled VE-siRNA and an epithelial permeability-enhancing compound.

FIG. 12 is a diagram illustrating the results of scanning electron microscopic observation of an ethylcellulose porous microsphere.

FIG. 13 is a diagram illustrating the shape of a suppository comprising Cy3-labeled VE-siRNA/p-MS.

FIG. 14 is a set of diagrams illustrating the results of confocal laser scanning microscopic observation of frozen sections prepared from the liver tissues of rats given rectal administration of substances such as a p-MS suppository preparation.

FIG. 15 is a set of diagrams illustrating the results of confocal laser scanning microscopic observation of frozen sections prepared from the large intestinal tissues of rats given rectal administration of substances such as a p-MS suppository preparation.

FIG. 16 is a graph illustrating the serum transthyretin concentration in mice given enema administration of substances such as VE-siRNA targeting the transthyretin gene and an epithelial permeability-enhancing compound.

MODE OF CARRYING OUT THE INVENTION

The pharmaceutical composition for transcolonic absorption of the present invention (hereinbelow, may also be simply expressed as "the pharmaceutical composition of the present invention") is characterized by comprising at least the following (a) and (b):
(a) a physiologically active substance having an intracellular site of action and bound with an introduction substance into lipoprotein (hereinbelow, may also be simply expressed as "the physiologically active substance of the present invention"), and
(b) a compound having an action of enhancing large intestinal mucosal epithelial permeability of the aforementioned physiologically active substance (hereinbelow, may also be simply expressed as "the compound having an epithelial permeability-enhancing action of the present invention.");

The pharmaceutical composition of the present invention can deliver the physiologically active substance of the present invention into specific tissue cells with high specificity by noninvasive administration of the pharmaceutical composition of the present invention to a subject in such a way that it is absorbed from the large intestinal tract. An overview of a conceivable delivery mechanism for the pharmaceutical composition of the present invention is illustrated in FIG. 1, in which a representative mode of the present invention is shown as an example. That is, FIG. 1 illustrates an overview of a case of delivery in which "Toc-siRNA" (α-tocopherol-bound siRNA) is used as the physiologically active substance of the present invention, a mixed micelle (MM) of linoleic acid (LA) and the surfactant HCO-60 is used as the compound having an epithelial permeability-enhancing action of the present invention, and an endogenous chylomicron is used as the lipoprotein of the present invention.

As illustrated in FIG. 1, when the pharmaceutical composition of the present invention (Toc-siRNA/MM) is administered in the form of a suppository or oral enteric agent, or by another route such as an oral drug delivery system, absorption of the physiologically active substance of the present invention (Toc-siRNA) from the mucosal epithelium of the large intestine (for example, the rectum) is accelerated by virtue of the action of the compound having an epithelial permeability-enhancing action (MM) of the present invention even when the physiologically active substance (siRNA) comprised in the pharmaceutical composition of the present invention is a poorly absorbable compound. The physiologically active substance of the present invention (Toc-siRNA) thus absorbed migrates into the lymphatic vessels and ascends along the lymphatic flow. Meanwhile, exogenous lipid derived from meal, etc. is converted into a lipoprotein such as a chylomicron (CM) in the mucosal epithelium of the small intestine. A chylomicron is then absorbed from the mucosal epithelium of the small intestine and transferred to nearby lymphatic vessels. The physiologically active substance of the present invention (Toc-siRNA) ascending in the lymphatic vessels meets a chylomicron in the lymphatic vessels near the small intestine, and then forms a complex (Toc-siRNA/CM) with the chylomicron via the moiety of introduction substance into lipoprotein (Toc) of the physiologically active substance of the present invention. The resulting complex (Toc-siRNA/CM) drains into the vein at the venous angle and is converted into a chylomicron remnant by lipoprotein lipase (LPL), which is then efficiently incorporated into the liver cells having the remnant receptor (LDL receptor or LRP-1 receptor) by endocytosis via the remnant receptor. A conceivable overview of the delivery mechanism for the pharmaceutical composition of the present invention is as descried above.

No particular limitation is imposed on the lipoprotein of the present invention as long as it is a lipoprotein present in vivo. However, preferable examples can include a chylomicron or a chylomicron remnant since it enables highly specific delivery into the liver cells. Among them, a chylomicron is given as a particularly preferable example.

No particular limitation is imposed on the aforementioned physiologically active substance of the present invention as long as it has an intracellular site of action and bound with an introduction substance into lipoprotein, and also, exerts its physiological activity in vivo. The physiologically active substance of the present invention may be either a synthetic substance or a naturally occurring substance. As the physiologically active substance, a commercially available product or an appropriately prepared product can be used. Among those physiologically active substances, preferable examples can include a molecular-targeted compound, an intracellular receptor ligand compound, and a compound acting on intracellular organelles. Among those physiologically active substances, more preferable examples can include those that do not have adverse effects in vivo or those that have adverse effects but within an acceptable range. Among those physiologically active substances, even more preferable examples can include poorly absorbable compounds that are poorly absorbed from the epithelium of the intestinal tract and having relatively high hydrophilicity. Among those physiologically active substances, still more preferable examples can include polynucleotides, polypeptides (including peptides), and modified forms or derivatives of polynucleotides and polypeptides. Specifically, still more preferable examples include molecular-targeted drugs and biological pharmaceutical products, for example nucleic acid drugs such as siRNA, shRNA, antisense oligonucleotides, antagomirs, nucleic acid aptamers, ribozymes, DNA decoys, and plasmids; peptide drugs such as hormones and cytokines; and antibody drugs. Among those physiologically active substances, still even more preferable examples can include nucleic acid drugs, of which siRNA can be given as a particularly preferable example. Specific examples of siRNA targeting the mouse apoB gene include siRNA consisting of a sense strand (27 mer) consisting of SEQ ID NO: 1 (5'-GUCAUCACACUGAAUACCAAUGCUGGA-3') and an antisense strand (29 mer) consisting of SEQ ID NO: 2 (5'-UCCAGCAUUGGUAUUCAGUGUGAUGA-CAC-3'). Also, specific examples of siRNA targeting the human transthyretin gene include siRNA consisting of a sense strand (27 mer) consisting of SEQ ID NO: 3 (5'-GUAACCAAGAGUAUUCCAUUUUUACUA-3') and an antisense strand (29 mer) consisting of SEQ ID NO: 4 (5'-UAGUAAAAAUGGAAUACUCUUGGUUACAC-3').

Further, the nucleic acid in the aforementioned nucleic acid drugs is preferably modified so as to acquire resistance to degradation in vivo. In particular, when the nucleic acid is RNA, it is preferable that the nucleic acid is subjected to an anti-RNase treatment such as methylation or thiophosphorylation so as to be resistant to degradation by intracellular RNases. Methylation treatment at the 2'-position of the ribose in a nucleic acid and thiophosphorylation treatment of the skeletal bond in a nucleic acid are more preferable. The number and position of nucleotide subjected to methylation or thiophosphorylation may affect the expression-suppressing activity of the nucleic acid to some extent, and therefore, there is a preferred mode as to the mode of the number, position, and the like of nucleotide to be subjected to methylation or thiophosphorylation. This preferred mode cannot be generalized because it also varies depending on the nucleic acid sequence to be modified; however, a preferred mode can be easily examined by confirming the expression-suppressing activity of the modified nucleic acid. For example, a preferred mode of anti-RNase treatment of the siRNA consisting of SEQ ID NOs: 1 and 2 mentioned above includes methylation at the 2'-position of the ribose in the nucleotides of the nucleotide numbers 2, 5, 11, 15, 21, 24 and 25 of the sense strand (SEQ ID NO: 1) and the nucleotides of the nucleotide numbers 1, 2, 5, 12, 14, 21, 24, 25, and 26 of the antisense strand (SEQ ID NO: 2), thiophosphorylation of the bond between the nucleotides of the nucleotide numbers 26 and 27 of the sense strand (SEQ ID NO: 1), and further, methylation at the 2'-position of the ribose and thiophosphorylation of the skeletal bond in the nucleotides of the nucleotide numbers 3, 4, 6, 27, and 28 of the antisense strand (SEQ ID NO: 2).

When the nucleic acid in the aforementioned nucleic acid drugs is a nucleic acid for suppressing the expression of the target gene, the "activity of suppressing the expression of the target gene" of the nucleic acid refers to the activity of reducing the intracellular expression of the target gene observed when the nucleic acid is introduced into the cell in comparison with the case in which the nucleic acid is not introduced. The reduced intracellular expression of the target gene can be examined by, for example, quantitating the target gene mRNA or proteins encoded by the target gene. For example, the degree of suppression of the expression of the target gene by the nucleic acid used in the present invention is such that, when the nucleic acid is introduced into a certain site in the intestinal tract at 0.1 to 50 mg/kg, the expression of the target gene in the destination tissue cells (preferably in the liver cells) is suppressed to 80% or less, more preferably 60% or less, even more preferably 40% or less, and still more preferably 20% or less at the mRNA level or at the protein level in comparison with the case in which the nucleic acid is not introduced.

When the aforementioned nucleic acid is siRNA, the number of nucleotides in the sense strand and/or antisense strand may be 21. Meanwhile, when the number is greater than 21, an intracellular Dicer cleaves the link between the aforementioned introduction substance into lipoprotein with a part of siRNA and the siRNA (of 21 nucleotides), whereby the resulting siRNA of 21 nucleotides can efficiently exert its expression-suppressing effect. Thus, the number of nucleotides is preferably greater than 21.

The aforementioned nucleic acid for suppressing the expression of the target gene can be designed by a publicly known method based on the information of, for example, the target gene sequence and the sequence of the potential transcription factor binding site. For example, a nucleic acid for suppressing the expression of the target gene can be designed using the method described in Japanese unexamined Patent Application Publication No. 2005-168485 when the nucleic acid is siRNA; by the method described in Nature, 1990, 346 (6287): 818 to 22 when the nucleic acid is a nucleic acid aptamer; and by the methods described in FEBS Lett, 1988, 239, 285; Protein, nucleic acid and enzyme, 1990, 35, 2191; and Nucl Acids Res, 1989, 17, 7059, and the like when the nucleic acid is a ribozyme. Further, an antisense oligonucleotide, an antagomir, and a DNA decoy can each be easily designed based on the information of the target gene sequence and the sequence of the potential transcription factor binding site.

The aforementioned nucleic acid can be prepared using, for example, a publicly known method. For example, an antisense oligonucleotide and a ribozyme can be prepared by determining the target sequence of mRNA or the initial transcription product based on the cDNA sequence or genomic DNA sequence of the target gene and synthesizing a sequence complementary to the target sequence using a commercially available DNA/RNA automatic synthesizer (Applied Biosystems, Beckman Coulter, Inc., and the like). Further, a DNA decoy or siRNA can be prepared by synthesizing each a sense strand and an antisense strand by a DNA/RNA automatic synthesizer, denaturing the strands in an appropriate annealing buffer solution at about 90° C. to about 95° C. for about one minute, and then allowing annealing to take place at about 30° C. to about 70° C. for about one to about eight hours, and the like. Further, a nucleic acid aptamer can be prepared by, for example, the method described in Japanese unexamined Patent Application Publication No. 2007-014292.

No particular limitation is imposed on the aforementioned introduction substance into lipoprotein according to the present invention as long as it is a hydrophobic compound or compound having a hydrophobic region that has an affinity with the aforementioned lipoprotein. However, preferable examples can include naturally occurring or synthetic fat-soluble molecules or their derivatives binding, preferably specifically, to a lipoprotein. Among those molecules or their derivatives, preferable examples can include those that do not have adverse effects in vivo or those that have adverse effects but within an acceptable range. Among those molecules or their derivatives, even more preferable examples can include lipid such as glyceride, cholesterol, glycolipid, and fatty acid; fat-soluble vitamins such as vitamin A, vitamin E, vitamin D, and vitamin K; intermediate metabolites such as acylcarnitine and acyl CoA; and their derivatives. Among those molecules or their derivatives, still more preferable examples can include vitamin E and cholesterol for their higher safety, of which vitamin E can be given as a particularly preferable example. It should be noted that the aforementioned introduction substance into lipoprotein can be used in combination of two or more of them.

Preferable examples of the aforementioned vitamin E include tocophenols represented by the following general formula (1) or tocotrienols represented by the general formula (2):

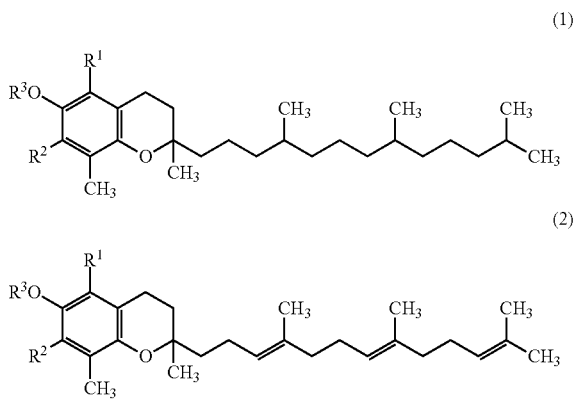

(wherein, $R^1$ and $R^2$ each represent a hydrogen atom or a methyl group and $R^3$ represents a hydrogen atom or a carboxylic acid residue) or a mixture comprising two or more of these compounds. Among these tocophenols and tocotrienols, α-tocopherol ($R^1$=a methyl group, $R^2$=a methyl group, and $R^3$=a hydrogen atom in the general formula (1)), β-tocopherol ($R^1$=a methyl group, $R^2$=a hydrogen atom, and $R^3$=a hydrogen atom in the general formula (1)), γ-tocopherol ($R^1$=a hydrogen atom, $R^2$=a methyl group, and $R^3$=a hydrogen atom in the general formula (1)), δ-tocopherol ($R^1$=a hydrogen atom, $R^2$=a hydrogen atom, and $R^3$=a hydrogen atom in the general formula (1)), α-tocotrienol ($R^1$=a methyl group, $R^2$=a methyl group, and $R^3$=a hydrogen atom in the general formula (2)), β-tocotrienol ($R^1$=a methyl group, $R^2$=a hydrogen atom, and $R^3$=a hydrogen atom in the general formula (2)), γ-tocotrienol ($R^1$=a hydrogen atom, $R^2$=a methyl group, and $R^3$=a hydrogen atom in the general formula (2)), δ-tocotrienol ($R^1$=a hydrogen atom, $R^2$=a hydrogen atom, and $R^3$=a hydrogen atom in the general formula (2)), and their acetate esters and succinate esters are preferable, of which α-tocopherol and γ-tocopherol are particularly preferable. Further, the d form, l form, and dl form are equally applicable as vitamin E.

The aforementioned introduction substance into lipoprotein and the aforementioned physiologically active substance may be connected by a direct bond or by an indirect bond via another substance intermediating between them. However, they are preferably directly connected by a chemical bond such as a covalent bond, an ionic bond, or a hydrogen bond, among which a covalent bond can be given as a particularly preferable example since it provides a more stable bond.

No particular limitation is imposed on the method for connecting the introduction substance into lipoprotein to the physiologically active substance. For example, when the introduction substance into lipoprotein is covalently bound to the physiologically active substance in the case that the physiologically active substance is a nucleic acid, it is preferable to connect the introduction substance into lipoprotein to the nucleic acid by a covalent bond in accordance with the method described in Tetrahedron Letters 33; 2729 to 2732, 1992. Also, when ionic binding or hydrogen binding is utilized, it is preferable to connect a positively-charged arginine residue to the introduction substance into lipoprotein and connect the positive charge of the arginine residue to the negative charge of the nucleic acid such as siRNA by ionic binding or hydrogen binding. Also, from the viewpoint of achieving further stable binding to the nucleic acid, the number of arginine residues to be connected to the introduction substance into lipoprotein is preferably two or more, more preferably three or more, and even more preferably four or more.

No particular limitation is imposed on the molecular weight of the physiologically active substance bound to the introduction substance into lipoprotein as long as the effects of the present invention are obtained. However, from the viewpoint of enjoying the benefits of the present invention to an especially great extent, preferable examples can include a molecular weight ranging from 1000 to 150000 Da. Within this range, more preferable examples can include a molecular weight ranging from 5000 to 100000 Da, and within this range, even more preferable examples can include a molecular weight ranging from 5000 to 50000 Da.

No particular limitation is imposed on the compound having an epithelial permeability-enhancing action of the present invention that is comprised in the pharmaceutical composition of the present invention as long as it is a compound having an action of enhancing the permeability of the physiologically active substance of the present invention through the mucosal epithelium of the large intestine. Among such compounds, preferable examples can include a compound enhancing the permeability of the physiologically active substance of the present invention across the intercellular space in the mucosal epithelium of the large intestine. Among such compounds, more preferable examples can include a compound having a high affinity with the introduction substance into lipoprotein according to the present invention. Among such compounds, even more preferable examples can include a compound that does not interfere with (preferably, a compound that promotes) the formation of a complex between the physiologically active substance of the present invention and the lipoprotein of the present invention in vivo. Among such compounds, still more preferable examples can include a compound that does not interfere with (preferably, a compound that promotes) the lymphatic transport of the physiologically active substance of the present invention. Among such compounds, still even more preferable examples can include a compound (a substance having no physiological activity is preferable) that is harmless to the living body at its effective dose and does not interfere with the physiological actions of the physiologically active substance of the present invention. Among such compounds, yet still more preferable examples can include a compound that is less harmful (preferably, a compound that is harmless) to the mucous membrane of the large intestine. Among such compounds, yet still more preferable examples can include a compound that forms a complex with the physiologically active substance of the present invention. Among such compounds, yet still more preferable examples can include a compound that can form a colloidal dispersion system (preferably a mixed micelle or an emulsion, more preferably a mixed micelle) with the physiologically active substance of the present invention when it is administered to a subject or when it penetrates through the mucosal epithelium of the large intestine in a subject. Specifically, a compound having a high affinity with the introduction substance into lipoprotein according to the present invention and having an action of enhancing the permeability of the physiologically active substance of the present invention through the mucosal epithelium of the large intestine (hereinbelow, may also be simply expressed as a "compound A") and a compound acting on a molecule involved in the tight junction of the intercellular space between epithelial cells or adhesion of epithelial cells or a compound acting on a molecule modulating the above molecule (hereinbelow, may also be simply expressed as a "compound B") can be given as preferable examples of the compound having an epithelial permeability-enhancing action of the present invention. Preferable examples of the aforementioned compound A can include naturally occurring or synthetic lipid and its derivative, a surfactant, and a peptide. Among these substances, more preferable examples can include a medium-chain fatty acid, a long-chain unsaturated fatty acid, monoglyceride, diglyceride, and their derivatives (preferably, a salt, an ester, or an ether), or a mixture thereof. Among these substances, even more preferable examples can include a medium-chain fatty acid, a long-chain unsaturated fatty acid, and their derivatives (preferably, a salt, an ester, or an ether) for their excellent epithelial permeability-enhancing action. Among these substances, particularly preferable examples can include a long-chain unsaturated fatty acid and its derivative (preferably, a salt, an ester, or an ether) since it not only has an excellent epithelial permeability-enhancing action, but also has a lipoprotein formation-enhancing action and a lymphatic flow rate-increasing action. Preferable examples of the aforementioned compound B include a claudin-4 regulatory factor, a chelating compound such as EDTA and citric acid, and a derivative thereof.

The aforementioned medium-chain fatty acid refers to a fatty acid having 8 to 12 carbon atoms. The aforementioned medium-chain fatty acid includes caprylic acid (octanoic acid), pelargonic acid (nonanoic acid), capric acid (decanoic acid), and lauric acid (dodecanoic acid). Among them, preferable examples can include capric acid and lauric acid, of which capric acid can be given as a more preferable example. Also, the aforementioned long-chain unsaturated fatty acid refers to an unsaturated fatty acid having 12 or more carbon atoms (preferably 12 or more and 30 or less, more preferably 12 or more and 24 or less, and even more preferably 14 or more and 20 or less), and it may be a monounsaturated fatty acid or a polyunsaturated fatty acid (preferably a divalent to octavalent unsaturated fatty acid, more preferably a divalent to hexavalent unsaturated fatty acid, even more preferably a divalent to tetravalent unsaturated fatty acid). Examples of the long-chain unsaturated fatty acid can include myristoleic acid (9-tetradecenoic acid), palmitoleic acid (9-hexadecenoic acid), oleic acid (cis-9-octadecenoic acid), elaidic acid (trans-9-octadecenoic acid), vaccenic acid (11-octadecenoic acid), linoleic acid (cis,cis-9,12-octadecadienoic acid), α-linolenic acid (9,12,15-octadecatrienoic acid), γ-linolenic acid (6,9,12-octadecatrienoic acid), pinolenic acid (5,9,12-octadecatrienoic acid), eleostearic acid (9,11,13-octadecatrienoic acid), stearidonic acid (6,9,12,15-octadecatetraenoic acid), gadoleic acid (9-icosenoic acid), eicosanoic acid (11-icosenoic acid), 8,11-icosadienoic acid, 5,8,11-icosatrienoic acid, arachidonic acid (5,8,11,14-icosatetraenoic acid), eicosapentaenoic acid (5,8,11,14,17-icosapentaenoic acid: EPA), erucic acid (13-docosenoic acid), docosadienoic acid (13,16-docosadienoic acid), adrenic acid (7,10,13,16-docosatetraenoic acid), osbond acid (4,7,10,13,16-docosapentaenoic acid), cervonic acid (docosahexaenoic acid: DHA), nervonic acid (cis-15-tetracosenoic acid), and tetracosapentaenoic acid (9,12,15,18,21-tetracosapentaenoic acid). Among them, more preferable examples can include oleic acid, linoleic acid, linolenic acid, docosahexaenoic acid, and eicosapentaenoic acid, of which linoleic acid can be given as a particularly preferable example.

No particular limitation is imposed on the aforementioned surfactant as long as it has an action of enhancing the permeability of the physiologically active substance of the present invention through the mucosal epithelium of the large intestine. Examples of the surfactant can include a nonionic surfactant such as HCO-60 (polyoxyethylene hydrogenated castor oil), polysorbate, polyethylene glycol, poloxamer, monoacylglycerol, monoacyl sorbitan, sucrose esters of fatty acids, and polyoxyethylene alkyl ether; and an anionic surfactant such as sodium lauryl sulfate. Among those surfactants, preferable examples can include a nonionic surfactant such as polyoxyethylene hydrogenated castor oil, polysorbate, polyethylene glycol, poloxamer, monoacylglycerol, monoacyl sorbitan, sucrose esters of fatty acids, and polyoxyethylene alkyl ether. Among those nonionic surfactants, more preferable examples can include polyoxyethylene hydrogenated castor oil, polysorbate, polyethylene glycol, poloxamer, monoacylglycerol, monoacyl sorbitan, and sucrose esters of fatty acids, of which polyoxyethylene hydrogenated castor oil can be given as a particularly preferable example.

It is to be noted the compound having an epithelial permeability-enhancing action of the present invention can be used in combination of two or more of them. For example, when a long-chain unsaturated fatty acid is used as the compound having an epithelial permeability-enhancing action of the present invention, it is preferable to concomitantly use a surfactant so as to allow the long-chain unsaturated fatty acid and the physiologically active substance of the present invention to form a complex (preferably a colloidal dispersion system, more preferably a mixed micelle or an emulsion, even more preferably a mixed micelle). Also, when a medium-chain fatty acid is used as the compound having an epithelial permeability-enhancing action of the present invention, it forms a complex with the physiologically active substance of the present invention even without the concomitant use of a surfactant; however, it is preferable to concomitantly use a surfactant for more thorough formation of a complex (preferably a colloidal dispersion system, more preferably a mixed micelle or an emulsion, even more preferably a mixed micelle).

Preferable examples of the large intestine in the aforementioned mucosal epithelium of the large intestine can include the colon (ascending colon, transverse colon, descending colon, and sigmoid colon) and the rectum, of which the rectum can be given as a particularly preferable example.

No particular limitation is imposed on the dosage form of the pharmaceutical composition of the present invention or its pharmaceutical preparation as long as it is an agent for transcolonic absorption. Preferable examples of the dosage form can include an agent for administration to the large intestine such as a suppository and an enema agent, an oral enteric agent, or an oral drug delivery system (oral drug delivery formulation) such as PULSINCAP (registered trademark) (WO 1990/009168), OROS (registered trademark) (F. Theeuwes, "OROS® Osmotic System Development", Drug Development and Industrial Pharmacy, 9 (7), pp. 1331 to 1357 (1983), F. Theeuwes "Systems for Triggered, Pulsed, and Programmed Drug Delivery", Novel Drug Delivery and Its Therapeutic Application, edited by L. F. Prescott and W. S. Nimmo, (Wiley, New York, 1989) pp. 323 to 340), and GI-MAPS (registered trademark) (Japanese unexamined Patent Application Publication No. 2005-272416). Here, it should be noted that transcolonic absorption includes, in addition to the absorption from the large intestine (including the colon, the rectum, etc.), the absorption from the lower section of the small intestine (the ileum).

When the pharmaceutical composition of the present invention is prepared as a pharmaceutical preparation, an appropriate pharmaceutically acceptable carrier, for example an arbitrary ingredient such as an excipient, a binder, a solvent, a solubilizing agent, a suspending agent, an emulsifier, a tonicity agent, a buffer, a stabilizer (preferably, a stabilizer for the physiologically active substance of the present invention), a pH adjuster, a colloidal stabilizer, a soothing agent, a preservative, an antioxidant, a thickener, a gelling agent, a colorant, a lubricant, a disintegrant, a humectant, an adsorbent, a sweetener, and a diluent can be mixed with the physiologically active substance of the present invention and the compound having an epithelial permeability-enhancing action of the present invention. Among those arbitrary ingredients, preferable examples can include a stabilizer for the physiologically active substance of the present invention, a pH adjuster, a colloidal stabilizer, an antioxidant, a thickener, and a gelling agent since the use of these ingredients can more strongly enhance the permeability of the pharmaceutical composition of the present invention through the mucosal epithelium of the large intestine. Also, it is preferable to further include, as an arbitrary ingredient, an agent for intracellular endosomal escape since the targeting of the physiologically active substance of the present invention to the intracellular target molecule can be enhanced.

Regarding a preferable mode of the pharmaceutical composition of the present invention or its pharmaceutical preparation, preferable examples can include a complex formed by the physiologically active substance of the present invention and the compound having an epithelial permeability-enhancing action of the present invention. Among such complexes, more preferable examples can include a complex in which a colloidal dispersion system is formed. Among such complexes, even more preferable examples can include a complex in which a mixed micelle or an emulsion is formed, of which a complex in which a mixed micelle is formed can be given as a particular preferable example. This is because the pharmaceutical composition of the present invention having a particularly excellent permeability through the mucosal epithelium of the large intestine can be obtained in this mode.

Also, a preferable example of the aforementioned products such as an agent for administration to the large intestine can include a pharmaceutical preparation obtained by preparing porous particles holding the pharmaceutical composition of the present invention as a suppository (hereinbelow, expressed as a "suppository comprising the porous particles"). This suppository has such advantages that production is simple and a protective effect can be imparted to the pharmaceutical composition of the present invention, and also, excessive dilution of the pharmaceutical composition of the present invention administered to the large intestine can be reduced.

No particular limitation is imposed on the suppository comprising the porous particles according to the present invention as long as it is a porous particle holding the pharmaceutical composition of the present invention. Also, any of the publicly known production methods (for example, a method of mixing a commercially available suppository base and a pharmaceutical composition) can be employed as the production method of the above suppository. However, preferable examples of the production method include the following "method for producing a suppository comprising the porous particles for application to the mucous membrane" in which a "compound or pharmaceutical composition for enema administration" (hereinbelow, may also be expressed as "substances such as a compound for enema administration") is used as the "compound or pharmaceutical composition for application to the mucous membrane" (hereinbelow, may also be expressed as "substances such as a compound for application to the mucous membrane" since production is simpler and a further excellent protective effect can be imparted to the pharmaceutical composition, and also, dilution of the pharmaceutical composition administered to the large intestine can be further reduced. It is to be noted that the aforementioned method was developed by the present inventors.

The aforementioned method for producing a suppository comprising the porous particles for application to the mucous membrane (hereinbelow, may also be expressed as a "suppository comprising the porous particles for application to the mucous membrane") includes dissolving substances such as a compound for application to the mucous membrane, which is a polar compound having a hydrophobic group, in a solvent, and immersing sponge-like porous particles consisting of hydrophobic polymers in the resulting solution, whereby the substances such as a compound for application to the mucous membrane are attracted to and held in the space within the porous particles to such an extent that the substances such as a compound for application to the mucous membrane can be released onto the mucous membrane after administration. The aforementioned compound for application to the mucous membrane is a polar compound having a hydrophobic group. Preferable examples of the physiologically active substance can include a physiologically active substance having an intracellular site of action and bound with an introduction substance into lipoprotein. Preferable examples of the aforementioned pharmaceutical composition for application to the mucous membrane can include a composition comprising the above physiologically active substance. The aforementioned physiologically active substance may be a polar compound to which a hydrophobic group is attached. Also, preferable examples of the aforementioned hydrophobic polymer can include alkyl celluloses such as methyl cellulose and ethyl cellulose, and also, an aminoalkyl methacrylate copolymer, an ethyl acrylate/methyl methacrylate/trimethylammonium ethyl methacrylate chloride copolymer, cellulose acetate phthalate, a methacrylic acid copolymer, hydroxypropylmethylcellulose phthalate, hydroxypropyl methylcellulose acetate succinate, and carboxy methyl ethyl cellulose. Among them, more preferable examples can include alkyl celluloses, and among those, ethyl cellulose can be given as an even more preferable example. No particular limitation is imposed on the form and particle diameter of the aforementioned porous particle as long as it can hold the aforementioned substances such as a compound for application to the mucous membrane. However, preferable examples of the form can include a column, a cube, and a sphere. Preferable examples of the particle diameter can include a range of 0.5 μm to 500 μm, within which more preferable examples can include a range of 5 μm to 50 μm. Preferable examples of the aforementioned hydrophobic group can include the compounds listed as examples of the introduction substance into lipoprotein above (for example, cholesterol and fat-soluble vitamin), and preferable examples of the aforementioned physiologically active substance can include the compounds listed as examples of the physiologically active substance above (for example, polynucleotide and polypeptide). Further, it is also possible to include a surfactant and an absorption enhancer into the space within the porous particle together with the substances such as compound for application to the mucous membrane so as to control release of the substances such as a compound for application to the mucous membrane from the porous particle in the suppository comprising the porous particles for application to the mucous membrane, dispersion after release, and absorption by the mucous membrane. Further, it is also possible to include an appropriate preserving agent and the like into the space within the porous particle together with the substances such as a compound for application to the mucous membrane to improve the storage stability of the suppository. For the method for producing the suppository comprising the porous particles for application to the mucous membrane, a common method for producing a suppository for application to the mucous membrane can be employed, except for using porous particles holding the substances such as a compound for application to the mucous membrane in place of the substances such as a compound for application to the mucous membrane. For example, a commercially available suppository base can be used. As the suppository base, for example, a suppository base manufactured by Gattefosse can be appropriately used according to the intended use. Also, no particular limitation is imposed on the product to be produced by the aforementioned method for producing the suppository comprising the porous particles for application to the mucous membrane as long as the suppository for application to the mucous membrane is produced, and preferable examples of the product to be produced can include a large intestinal suppository such as a rectal suppository, a vaginal suppository, and a urethral suppository. Also, when a porous particle consisting of water-soluble polymers is used, a polar compound will be used as the substances such as a compound for application to the mucous membrane. Regarding this point, the porous particle has a high affinity to the substances such as a compound for application to the mucous membrane, and although the dispersion within the suppository can be secured, it is difficult to separately control the release of the porous particle from the suppository after administration and the release of the substances such as a compound for application to the mucous membrane from the porous particle. Thus, a protective action of the porous particle on the substances such as a compound for application to the mucous membrane, which are unstable in the mucous membrane of the digestive tract and the like, is either lost or insufficient. Furthermore, because the compound for application to the mucous membrane is diluted in the mucous membrane to which the compound is administered, absorption by passive transport will be reduced. In contrast, when porous particles consisting of hydrophobic polymers and a polar compound having a hydrophobic group (the substances such as a compound for application to the mucous membrane) are used, a protective effect can be imparted to the substances such as a compound for application to the mucous membrane by the porous particle and dilution in the mucous membrane to which the suppository is administered can be reduced even after the release of the porous particle from the suppository after administration by adjusting the affinity between the porous particle and the substances such as a compound for application to the mucous membrane by selecting, adjusting, or performing any other action on the hydrophobic group of the substances such as a compound for application to the mucous membrane.

The contents of the physiologically active substance of the present invention and the compound having an epithelial permeability-enhancing action of the present invention in the pharmaceutical composition of the present invention can be set at any desired amount by adding a release amount-regulatory mechanism (such as a release-controlling membrane) to a pharmaceutical preparation. Although no particular limitation is imposed on the contents of the above substances as long as the effects of the present invention are obtained, as preferable examples, the concentrations of the above substances in the digestive tract are each independently in a range of preferably 0.1 μM to 1000 mM, more preferably 10 μM to 50 mM. For example, in view of the above, when the pharmaceutical composition of the present invention is a liquid agent, the above concentrations are each in a range of preferably 0.1 μM to 1000 mM, more preferably 10 μM to 50 mM, as preferable examples.

No particular limitation is imposed on the molar ratio of the physiologically active substance of the present invention to the compound having an epithelial permeability-enhancing action of the present invention comprised in the pharmaceutical composition of the present invention as long as the effects of the present invention are obtained. However, as preferable examples, the molar ratio is in a range of 1:1000 to 1000:1, as more preferable examples, the ratio is in a range of 1:100 to 100:1, and as even more preferable examples, the molar ratio is in a range of 1:10 to 10:1.

From the viewpoint of improving the efficiency of delivery of the physiologically active substance of the present invention into tissue cells to obtain greater physiological activity of the physiologically active substance of the present invention, the pharmaceutical composition of the present invention is preferably administered to a vertebrate under the condition that the production of endogenous lipoprotein (preferably, chylomicron) has been induced in vivo. No particular limitation is imposed on the condition that the production of endogenous lipoprotein (preferably, chylomicron) has been induced as long as the above object can be achieved; however, a condition of within 12 hours (for example, within 10 hours, within eight hours, within six hours, within four hours, within two hours, and within one hour) after oral administration of lipid to a vertebrate is preferable. The lipid may be orally administered either as lipid itself or in the form of a lipid-containing meal. It is more preferable to render a subject of administration in a state of starvation by a means such as fasting prior to induction of the production of endogenous lipoprotein (preferably, chylomicron). The detail of the mechanism of action in which the efficiency of cellular uptake of the physiologically active substance of the present invention is improved by administering a lipid and/or further rendering a subject of administration in a state of starvation in advance of the administration remains unknown. However, considering the fact that the LRP-1 receptor on liver cells, which is involved in the lipoprotein uptake, is known to be expressed at a higher level on the cell membrane and activated by oral ingestion of lipid and by insulin (Mol. Pharmacol. 2007 Jul.

3; 17609417), it is speculated that lipid ingestion, etc. increases the expression level of the receptor involved in lipoprotein uptake or activates the above receptor, leading to increased introduction of lipoprotein (preferably chylomicron) into liver cells, thereby improving the efficiency of uptake of the physiologically active substance of the present invention bound to the introduction substance into lipoprotein by liver cells. It should be noted that the aforementioned state of starvation refers to a state in which a subject has not ingested any food or drink (except a calorie-free drink or food such as water) for a certain period of time, and examples of such a state include a state in which no food has been given to a subject of administration for six hours or more, preferably for eight hours or more, more preferably 12 hours or more, and even more preferably 24 hours or more.

Also, the pharmaceutical composition of the present invention is a pharmaceutical composition that is absorbed from the large intestinal tract and is administered orally or parenterally according to the aforementioned dosage form. That is, an oral DDS formulation such as an oral enteric agent can be orally ingested, while an agent for administration to the large intestine such as a suppository and an enema agent can be inserted or injected through the anus.

The dose of the pharmaceutical composition of the present invention varies according to factors such as the age, body weight, and symptoms of the subject of administration, the type of disease affecting the subject of administration, and the kind of the physiologically active substance of the present invention comprised in the pharmaceutical composition; however, the pharmaceutical composition can be administered for example, at 0.1 to 30 mg/kg in one to three divided doses per day.

No particular limitation is imposed on the disease for which the pharmaceutical composition of the present invention is administered as long as it is a disease attributable to some abnormality in physiological activities (preferably, increase or decrease) that can be improved by the physiologically active substance of the present invention. Preferable examples of the disease attributable to abnormality in physiological activities include familial amyloid neuropathy attributable to the expression of a mutant transthyretin gene. Also, preferable examples of a disease attributable to hyperactivation of a specific gene include viral hepatitis and liver cancer attributable to enhanced expression of the hepatitis virus gene.

No particular limitation is imposed on the subject of administration in the present invention as long as it is an animal. However, preferable examples include vertebrates. More preferable examples include animals belonging to mammals or birds. Among those animals, even more preferable examples include animals belonging to mammals. Among those animals, still more preferable examples include humans, rats, mice, pigs, rabbits, dogs, cats, monkeys, horses, cows, goats, and sheep, among which humans can be given as a particular preferable example.

Further, the pharmaceutical composition of the present invention can also be used as the active ingredient of an agent for administration to the large intestine or an oral enteric agent.

No particular limitation is imposed on a method for delivering the physiologically active substance of the present invention into a specific tissue cell (hereinbelow, may also be referred to as "the delivery method of the present invention") as long as it comprises the step (X) of administering the aforementioned pharmaceutical composition of the present invention to a vertebrate so that it is absorbed from the large intestinal tract. However, from the viewpoint of improving the efficiency of delivery of the physiologically active substance of the present invention into tissue cells to obtain greater physiological activity of the physiologically active substance of the present invention, it is preferable to administer the pharmaceutical composition under the condition that the production of endogenous lipoprotein (preferably, chylomicron) has been induced in vivo.

The method of administration in the aforementioned step (X) can be carried out by a method similar to that applied for the aforementioned pharmaceutical composition of the present invention.

No particular limitation is imposed on the tissues and cells to which the physiologically active substance of the present invention can be delivered by the delivery method of the present invention as long as they are the tissues and cells to which the lipoprotein of the present invention migrates in vivo. However, when the lipoprotein is a chylomicron or a chylomicron remnant, delivery to liver tissue cells (preferably, liver parenchymal cells) and liver cancer cells can be given as examples of a particularly preferable mode since the physiologically active substance of the present invention can be delivered into the aforementioned cells with high specificity.

It should be noted that the delivery method of the present invention can be used also as the disease treatment method of the present invention by applying it to an affected animal or patient.

Examples of other modes of the preset invention include the use of the physiologically active substance of the present invention and the compound having an epithelial permeability-enhancing action of the present invention for the preparation of the pharmaceutical composition for transcolonic absorption (or a disease treatment agent) of the present invention; and the use of the physiologically active substance of the present invention and the compound having an epithelial permeability-enhancing action of the present invention for the treatment of a disease.

Hereinbelow, the present invention will be described in detail with reference to Examples; however, the present invention is not limited to these Examples.

EXAMPLES

Example 1

Synthesis of Vitamin E-Bound Small Interfering RNA (VE-siRNA)

As one example of the physiologically active substance of the present invention, siRNA targeting the mouse apoB gene was produced. Specifically, siRNA consisting of a sense strand (27 mer) consisting of SEQ ID NO: 1 (GUCAUCA-CACUGAAUACCAAUGCUGGA) and an antisense strand (29 mer) consisting of SEQ ID NO: 2 (UCCAGCAUUG-GUAUUCAGUGUGAUGACAC) was synthesized and then subjected to appropriate chemical modification. To the 5'-end of the antisense strand of the resulting siRNA, α-tocopherol (Toc), which is one of the naturally occurring isomers of vitamin E, was covalently bound as an introduction substance into lipoprotein by a phosphate bond, whereby VE-siRNA was obtained (FIG. 2).

Example 2

Study of the Delivery of Fluorescently-Labeled VE-siRNA to the Liver Tissues 1

In order to examine if the physiologically active substance can be efficiently delivered to the liver tissues according to the present invention, the following study was conducted.

(1) Preparation of Pharmaceutical Preparations

As a permeability-enhancing agent, linoleic acid (LA) (the product of Wako Pure Chemical Industries, Ltd.) was prepared, and as a surfactant, HCO-60 (the product of Nikko Chemicals Co., Ltd.) was prepared. Using HCO-60 (3.0 w/w %) and RNase-free phosphate buffered saline (PBS), the final dose level of LA was adjusted to be 10 mM, followed by sonication using a sonicator, whereby a preparation-at-use mixed micelle was prepared. The pH of the resulting preparation-at-use mixed micelle was adjusted to be 7.4 with 0.1 N NaOH. The preparation-at-use mixed micelle and fluorescence (Cy3)-labeled VE-siRNA (0.3 mg/head) were thoroughly mixed by pipetting, whereby a pharmaceutical preparation of Example (HCO-60/LA/VE-siRNA) (pharmaceutical preparation E) to be used for a delivery study was prepared.

Also, as a control, PBS (pharmaceutical preparation A); a pharmaceutical preparation (HCO-60/LA/PBS) (pharmaceutical preparation B) comprising a mixture of the aforementioned preparation-at-use mixed micelle and PBS; a pharmaceutical preparation (HCO-60/LA/siRNA) (pharmaceutical preparation C) comprising a mixture of the aforementioned preparation-at-use mixed micelle and fluorescence (Cy3)-labeled siRNA (0.3 mg/head); and a pharmaceutical preparation (HCO-60/PBS/VE-siRNA) (pharmaceutical preparation D) comprising a mixture of a preparation-at-use mixed micelle prepared using HCO-60 and PBS, and fluorescence (Cy3)-labeled VE-siRNA (0.3 mg/head) were each prepared.

(2) Rectal Administration of the Pharmaceutical Preparations to Animals

Mice (ICR, 9-week-old) were prepared as animals to which the pharmaceutical preparations prepared in the aforementioned Example 2 (1) were administered. After fasting overnight, the mice were given oral administration of 0.4 ml of milk with 5% milk fat three times with 30-minute intervals to promote the chylomicron formation. Thirty minutes after the last milk administration, the mice were anesthetized with Nembutal and the intestinal tract was washed. Subsequently, the aforementioned pharmaceutical preparations were each administered (about 200 μL) through the anus (rectal administration) as enema agents, and the anus was ligated. Residual drugs in the intestine were removed every two hours after single administration of the pharmaceutical preparations, followed by additional administration of the same dose of the pharmaceutical preparations. Administration was conducted three times in total. Further, with regard to the pharmaceutical preparation of Example (pharmaceutical preparation E), the following administrations were conducted in addition to the above. That is, the pharmaceutical preparation E was similarly rectally administered without pre-administration of milk after fasting (Milk(−) HCO-60/LA/VE-siRNA) and pre-administration of milk was similarly given after fasting and a solution of Triton-X100 (the product of Sigma) diluted with physiological saline (20 mg/kg) was administered via the tail vein 30 minutes before rectal administration of the pharmaceutical preparation E (Triton-X pre i.V. HCO-60/LA/VE-siRNA).

(3) Confocal Microscopic Observation of the Distribution of siRNA in the Liver

In the aforementioned Example 2 (2), the mice were anesthetized and subjected to perfusion with physiological saline of 4° C. two hours after the last administration of the pharmaceutical preparations, followed by excision of the liver. The liver thus excised was fixed overnight in 4% paraformaldehyde (the product of Wako Pure Chemical Industries, Ltd.), and then fixed overnight in 30% sucrose (the product of Wako Pure Chemical Industries, Ltd.). The liver was then embedded in the O.C.T. Compound (the product of Sakura Finetek Japan Co., Ltd.) and frozen sections were prepared in accordance with a routine method. The frozen sections were then each subjected to staining of cell nuclei and cell fibers using the TO-PRO(registered trademark)-3 (the product of Molecular Probe) and the Fluorescein (FITC)-phalloidin (the product of Invitrogen). The results of the confocal laser scanning microscopic observation of these frozen sections are shown in FIG. 3. FIG. 3 A shows the results of administration of the pharmaceutical preparation A, FIG. 3 B shows the results of administration of the pharmaceutical preparation B, FIG. 3 C shows the results of administration of the pharmaceutical preparation C, FIG. 3 D shows the results of administration of the pharmaceutical preparation D, FIG. 3 E shows the results of administration of the pharmaceutical preparation E, FIG. 3 F shows the results of administration of the pharmaceutical preparation E without pre-administration of milk after fasting, and FIG. 3 G shows the results of administration of the pharmaceutical preparation E after administration of the Triton-X100 solution. Also, panels shown in FIG. 3 A to G are each divided in quarters, in which the upper left quarter indicates the results of detection of blue fluorescence of TO-PRO(registered trademark)-3, the upper right quarter indicates the results of detection of green fluorescence of FITC-phalloidin, the lower left quarter indicates the results of red fluorescence of Cy3, and the lower right quarter indicates the results of the superimposition of the results of detection of fluorescence in the upper left quarter, upper right quarter, and lower left quarter.

In the groups A and B, in which the pharmaceutical preparation A (PBS) and the pharmaceutical preparation B (HCO-60/LA/PBS) were administered as a control, respectively, fluorescence based on Cy3 was almost not observed (FIGS. 3 A and B). In contrast, in the group E, in which the pharmaceutical preparation E (HCO-60/LA/VE-siRNA), which is a mixed micelle of HCO-60/LA (a compound having an epithelial permeability-enhancing action) and fluorescence (Cy3)-labeled VE-siRNA, was administered, marked fluorescence based on Cy3 was observed (FIG. 3 E) The above results showed that siRNA, which is the physiologically active substance, was successfully and efficiently delivered into liver parenchymal cells enterally by preparing siRNA as the pharmaceutical composition for enteral absorption according to the present invention.

Also, in the group D, in which the pharmaceutical preparation D (HCO-60/PBS/VE-siRNA), which is the pharmaceutical preparation E (pharmaceutical preparation of Example) lacking LA, was administered, fluorescence based on Cy3 was almost non-detectable (FIG. 3 D). The above results showed that the fatty acid LA in HCO-60/LA, which is an epithelial permeability-enhancing agent, was one of the essential factors for delivery of VE-siRNA from the intestinal tract into the liver cells.

Also, in the group C, in which the pharmaceutical preparation C prepared using fluorescence (Cy3)-labeled siRNA in place of fluorescence (Cy3)-labeled VE-siRNA in the pharmaceutical preparation E (pharmaceutical preparation of Example) was administered, fluorescence based on Cy3 was almost non-detectable (FIG. 3 C). The above results showed that binding of VE, which is an introduction substance into lipoprotein, to siRNA was one of the essential factors for delivery of siRNA from the intestinal tract into the liver cells.

Further, also in the group F (Milk(–) HCO-60/LA/VE-siRNA), in which the pharmaceutical preparation E (pharmaceutical preparation of Example) was rectally administered without pre-administration of milk after fasting, fluorescence based on Cy3 was observed but not as intensely as in the group E, in which pre-administration of milk was performed (FIG. 3 F). Considering that pre-administration of milk promotes the chylomicron formation, the above results showed that the efficiency of delivery of VE-siRNA from the intestinal tract into the liver cells was improved by an increase in the amount of chylomicron formation. The above results showed that formation of chylomicrons in vivo was one of the essential factors for delivery of siRNA from the intestinal tract into the liver cells.

Also, in the group G (Triton-X pre i.V. HCO-60/LA/VE-siRNA), in which pre-treatment with Triton-X100 was administered, fluorescence based on Cy3 was almost non-detectable (FIG. 3 G). That is, despite the fact that pre-administration of milk was performed in the group G, delivery of VE-siRNA from the intestinal tract into the liver cells was clearly inhibited in comparison with the group E. Considering that Triton-X100 has an inhibitory activity on the formation of remnants from chylomicrons, the above results have suggested that there is a correlation between the migration of siRNA to the liver and the migration of chylomicrons in the form of remnants to the liver. In light of this, the above results showed that the formation of remnants from chylomicrons was one of the essential factors for delivery of siRNA from the intestinal tract into the liver cells.

Example 3

Confirmation Study for Uptake of Fluorescently-Labeled VE-siRNA by the Mouse Lymph Fluid 1

In order to examine the mechanism of delivery of the physiologically active substance of the present invention to the liver tissues, the following study was conducted.

Mice (ICR, 9-week-old) were prepared. The mice were fasted for 16 hours and then given oral administration of 0.4 ml of milk with 5% milk fat three times with 30-minute intervals to promote the chylomicron formation. Thirty minutes after the last milk administration, the mice were anesthetized with Nembutal and the intestinal tract was washed. Subsequently, about 200 µL of the pharmaceutical preparation E (HCO-60/LA/VE-siRNA) described in the aforementioned Example 2 was administered through the anus (rectal administration) as an enema agent, and the anus was ligated. Two hours after single administration of the aforementioned pharmaceutical preparation, the lymph fluid was obtained from the intestinal lymphatic vessels of the mice. The diffusion time of the Cy3-labeled molecules in the lymph fluid was obtained by fluorescence correlation spectroscopy (FCS). Also, as a control, FCS was similarly performed using fluorescence (Cy3)-labeled VE-siRNA in place of the pharmaceutical preparation E (HCO-60/LA/VE-siRNA). The results of the above FCS are shown in FIG. 4.

As understood from the results of FIG. 4, when the pharmaceutical preparation E was administered, the diffusion time of fluorescence based on Cy3 was markedly increased to about 2500 microseconds in comparison with the administration of the control. These results suggest that fluorescence (Cy3)-labeled VE-siRNA is taken up in a greater amount by molecules of equivalent size to chylomicrons in the mouse lymph fluid by virtue of HCO-60/LA (a compound having an epithelial permeability-enhancing action).

Example 4

Confirmation Study for Uptake of Fluorescently-Labeled VE-siRNA by the Mouse Lymph Fluid 2

Mice (ICR, 9-week-old) were prepared. The mice were fasted for 16 hours and then given oral administration of 0.4 ml of milk with 5% milk fat three times with 30-minute intervals to promote the chylomicron formation. Thirty minutes after the last milk administration, the mice were anesthetized with Nembutal and the intestinal tract was washed. Subsequently, the distal part of the intestinal tract or the anus was ligated to create a loop of intestinal tract, and through the anus part of the loop, the pharmaceutical preparation E (HCO-60/LA/VE-siRNA) described in the aforementioned Example 2 was administered at 10 mg/kg.

Two hours after the last administration, the lymph fluid was obtained from the intestinal lymphatic vessels of the mice. The diffusion time of the Cy3-labeled molecules was obtained by fluorescence correlation spectroscopy (FCS). Also, the lymph fluid obtained from an untreated mouse was fractionated into lipoprotein fractions by high-performance liquid chromatography (HPLC) and the diffusion time of the resulting fractions was obtained by a similar manner and compared with that from the treated mouse. The results thus obtained are shown in FIG. 5.

From the results of FIG. 5, the diffusion time of Cy3-bound particles was found to be about 3000 µs, which was consistent with the diffusion time of the chylomicron fraction fractionated from the lymph fluid by HPLC. These results show that VE-siRNA administered to the rectum enters into the lymphatic vessels via absorption, where it is bound to chylomicrons.

Example 5

Northern Blot Analysis for the Detection of the Antisense Strand of Rectally Administered VE-siRNA In order to examine the mechanism of delivery of the physiologically active substance of the present invention to the liver tissues, the following Northern blot analysis was successively performed.

First of all, as the mice to which the physiologically active substance was administered, the wild-type mouse and three types of mice in which proteins associated with the main receptors for chylomicron were knocked out were prepared. That is, the wild-type mouse (Wild type), a LDL receptor-knock-out mouse (LDLR KO), a receptor associated protein (RAP)-knock-out mouse (RAPKO), and an ApoE-knock-out mouse (ApoE KO) were prepared. The main receptors for chylomicron include LDL receptor and LRP-1 receptor, while RAP has a competitive inhibitory action on the LRP-1 receptor. Also, ApoE is one of the natural ligands for LRP-1 receptor, and it is present in chylomicron, not in the cell membrane.

A mixture (HCO-60/LA/VE-siRNA) of VE-siRNA and a mixed micelle (HCO-60/LA) was rectally administered to each of the aforementioned mice three times with 2-hour intervals, and two hours after the last administration, the liver was excised from each mouse. The method of rectal administration and the method of excision of the liver were performed in accordance with the method described in Example 2. Also, with regard to the LDL receptor-knock-out mouse, a group in which intravenous injection of RAP was administered before the rectal administration of HCO-60/LA/VE-siRNA was also prepared in addition to a group in which HCO-60/LA/VE-siRNA was rectally administered.

From the cells from the aforementioned excised liver, total RNA was extracted in accordance with a routine method. The total RNA thus extracted (10 µg) was subjected to electrophoresis in 14% polyacrylamide gel, and then transferred to a nylon membrane. Meanwhile, as a probe hybridizing to the antisense strand of the VE-siRNA administered, a probe having an identical sequence to the sense strand of VE-siRNA was prepared. This probe was fluorescently labeled with fluorescein using the Gene Images 3'-Oligolabelling Kit (the product of Amersham Biosciences). The fluorescently labeled probe thus obtained was allowed to react with the aforementioned nylon membrane and the fluorescence of fluorescein was detected by the Gene Images CDP-star detection Kit (the product of Amersham Biosciences). The results thus obtained are shown in FIG. 6.

In the lane (1) (Wild type), which represents the wild-type mouse given rectal administration of HCO-60/LA/VE-siRNA, two bands representing 21 nucleotides (nt) and 29 nt were clearly detected, of which the 21 nt was more intense. Considering that the antisense strand of the VE-siRNA administered is 29-mer-long and cleavage of VE-siRNA by cytosolic Dicer generates a 21-mer-long mature siRNA antisense strand, the above results show that the VE-siRNA administered has been taken up as far as into the cytoplasm of the liver cells.

Meanwhile, in the lane (3) (LDLR KO), lane (4) (RAP KO), and lane (5) (ApoE KO), which represent the three types of rectally-administered mice in which proteins associated with the main receptors for chylomicron were knocked out, a reduced concentration of band was noted in comparison with the lane (1). Particularly in the lane (2) representing the rectally-administered LDL receptor-knock-out mouse (LDLR KO) that was given intravenous administration of RAP having a competitive inhibitory action on the LDL receptor and the LRP-1 receptor, the bands were very faint to almost absent. These results are considered to be suggestive of uptake of rectally administered HCO-60/LA/VE-siRNA by the liver cells via the LDL receptor and the LRP-1 receptor.

Taking the results of Example 5 into consideration with the results of Examples 2 to 4 described above, the following delivery mechanism was speculated. That is, upon administration of VE-siRNA to the rectum in the form of a mixed micelle, it penetrates through the epithelium of the intestinal tract by virtue of the epithelial permeability-enhancing action of LA. Subsequently, VE-siRNA migrates into and ascends in the lymphatic vessels. During this migration, VE-siRNA meets chylomicrons produced by the epithelial cells of the small intestine and secreted into the lymphatic vessels, and forms a complex with chylomicrons via the part that is modified with VE, which is an introduction substance into lipoprotein. The resulting VE-siRNA-chylomicron complex drains into the vein at the venous angle and is converted into chylomicron remnants by lipoprotein lipase (LPL), and then taken up by the liver cells having the remnant receptor (LDL receptor and LRP-1 receptor).

Example 6

Quantitative RT-PCR for Confirmation of the Sequence-Specific Gene Expression Suppression Effect of the VE-siRNA Administered In order to examine if the physiologically active substance of the present invention is delivered to the liver tissues and actually exerts its function in the cells, the following quantitative RT-PCR was performed.

HCO-60/LA/VE-siRNA was rectally administered to mice three times with 2-hour intervals, and 24 hours after the last administration, the liver was excised from the mice. The method of rectal administration and the method of excision of the liver were performed in accordance with the method described in Example 2. From the cells from the aforementioned excised liver, total RNA was extracted according to a routine method. Using 2 µg of the total RNA thus obtained, its complementary DNA (cDNA) was synthesized. Using the cDNA thus obtained as a template, quantitative RT-PCR was performed in accordance with a routine method using a primer/probe for the gene targeted by the aforementioned VE-siRNA (apoB gene). Meanwhile, as an endogenous control, quantitative RT-PCR was similarly performed on an endogenous gene not targeted by the aforementioned VE-siRNA. Also, only a mixed micelle (HCO-60/LA) was rectally administered in place of HCO-60/LA/VE-siRNA and quantitative RT-PCR was similarly performed. From the results of the above quantitative RT-PCR, the ratio of the expression level of the target gene to the expression level of the endogenous gene in each mouse (at the relative target mRNA level) was obtained. The relative target mRNA level was compared between the mouse administered with VE-siRNA (mixed micelle+VE-siRNA) and the mouse administered only with a mixed micelle (mixed micelle only). The results thus obtained are shown in FIG. 7.

As understood from the results of FIG. 7, in comparison with the group in which only a mixed micelle (HCO-60/LA) was administered, the expression of the target gene was successfully suppressed by about 40% in the group in which HCO-60/LA/VE-siRNA was administered (FIG. 7). These results suggested that upon administration to the rectum, the physiologically active substance of the present invention was delivered to the liver tissues and actually exerted its function (physiological activity) in the cells.

Example 7

Western Blot Analysis for Confirmation of the Sequence-Specific Gene Expression Suppression Effect of the VE-siRNA Administered In order to examine if the physiologically active substance of the present invention is delivered to the liver tissues and actually exerts its function in the cells, the following Western blot analysis was performed.

HCO-60/LA/VE-siRNA was rectally administered to mice three times with 2-hour intervals. The method of rectal administration was performed in accordance with the method described in Example 3. Twenty four hours after the last administration, the mouse serum was obtained and adjusted using a homogenizing buffer (0.1% SDS, 1% TritonX, 1% sodium deoxycholate, and 1 mM PMSF), whereby samples were prepared. As the primary antibody, a 500-fold dilution of sc11795 goat anti-ApoB (the product of Santa Cruz Biotechnology, Inc.) was used. Also, as the secondary antibody, a 2000-fold dilution of sc2020 donkey anti-goat (the product of Santa Cruz Biotechnology, Inc.) was used. The Supersignal West Femto Maximum Sensitivity Substrate (the product of Thermo Fisher Scientific K. K.) was used for fluorescent color development of the sample, which was photographed by the Chemi Doc XRS-J (the product of Bio-Rad Laboratories, Inc.). From the results of detection, the concentration of band was quantitated and the apoB100/48 ratio was obtained. The apoB100/48 was compared between the mouse administered with VE-siRNA and the mouse administered only with a mixed micelle. The results thus obtained are shown in FIG. 8 A and B.

As understood from the results of FIGS. 8 A and B, in comparison with the group in which only a mixed micelle was administered, the protein expressed by the target gene was reduced by about 74% in the group in which HCO-60/LA/VE-siRNA was administered. These results demonstrated, also at the protein level, that upon administration to the rectum, the physiologically active substance of the present invention was delivered to the liver tissues and actually exerted its function in the cells.

Example 8

Measurement of the Triglyceride and LDL Cholesterol Levels in the Serum for Confirmation of the Sequence-Specific Gene Expression Suppression Effect of the VE-siRNA Administered In order to examine if the physiologically active substance of the present invention is delivered to the liver tissues and actually exerts its function in the cells, the following analysis was successively performed.

HCO-60/LA/VE-siRNA was rectally administered to mice three times with 2-hour intervals. The method of rectal administration was performed in accordance with the method described in Example 3. Twenty four hours after the last administration, the mouse serum was obtained, in which the triglyceride and LDL cholesterol levels were measured. The results thus obtained are shown in FIG. 9.

As understood from the results of FIG. 9, in comparison with the group in which only a mixed micelle was administered, the serum triglyceride level and the serum LDL cholesterol level were both reduced by about 40% in the group in which HCO-60/LA/VE-siRNA was administered. These results showed that upon administration to the rectum, the physiologically active substance of the present invention was delivered to the liver tissues and actually exerted its function in the cells, thereby effectively functioning as a serum lipid-suppressing drug.

Example 9

Study of the Delivery of Fluorescently-Labeled VE-siRNA to the Liver Tissues 2

In order to examine if the physiologically active substance can be efficiently delivered to the liver tissues even when a compound having an epithelial permeability-enhancing action other than HCO-60/LA is used, the following study was conducted.

A study of the delivery to the liver tissues was performed by a method similar to that described in Example 2 except for using, in place of the pharmaceutical preparation E (HCO-60/LA/VE-siRNA), a pharmaceutical preparation (DHA/HCO-60/VE-siRNA), in which "LA" in the pharmaceutical preparation E was replaced by "DHA" (the product of Cayman Chemical Company) (FIG. 10 A); a pharmaceutical preparation (Sodium Caprate/VE-siRNA), in which "HCO-60/LA" in the pharmaceutical preparation E was replaced by sodium caprate (the product of Sigma, final concentration of 15 mM) (FIG. 10 B); a pharmaceutical preparation (Citric acid/VE-siRNA), in which "HCO-60/LA" in the pharmaceutical preparation E was replaced by citric acid (the product of Nacalai Tesque, Inc., final concentration of 20 mM) (FIG. 10 C); and a pharmaceutical preparation (Labrasol/VE-siRNA), in which "HCO-60/LA" in the pharmaceutical preparation E was replaced by the surfactant Labrasol (registered trademark) (the product of GATTEFOSSE; 2 w/v %), namely PEG-8 capryl/caprylic acid glyceride (FIG. 10 D). The results of confocal laser scanning microscopic observation of frozen sections prepared from the mouse liver tissues in this delivery study are shown in FIG. 10 A to D. Also, the panels A to D shown in FIG. 10 are each divided in quarters, in which the upper left quarter indicates the results of detection of blue fluorescence of TO-PRO (registered trademark)-3, the upper right quarter indicates the results of detection of green fluorescence of FITC-phalloidin, the lower left quarter indicates the results of detection of red fluorescence of Cy3, and the lower right quarter indicates the results of the superimposition of the results of detection of fluorescence in the upper left quarter, upper right quarter, and lower left quarter.

As understood from the results of FIG. 10 A to D, it was revealed that even when a compound having an epithelial permeability-enhancing action other than HCO-60/LA was used, although there was a variation in the delivery efficiency, the physiologically active substance was successfully delivered to the liver tissues. However, when the surfactant Labrasol (registered trademark) was used, although migration to the liver tissues was observed, little delivery into the liver parenchymal cells was observed (FIG. 10 D). When citric acid, which is a chelating agent, was used, the facilitatory effect on the delivery to the liver parenchymal cells was comparable to that observed with the use of HCO-60/DHA (long-chain unsaturated fatty acid) (FIG. 10 A). When sodium caprate (a medium-chain fatty acid salt) was used, the best facilitatory effect on the delivery to the liver parenchymal cells was achieved. Also, although the results are not shown in the Figures, in comparison with the use of HCO-60/DHA, an equivalent or better delivery-facilitating effect was exhibited also when HCO-60/EPA (long-chain unsaturated fatty acid) or HCO-60/oleic acid (long-chain unsaturated fatty acid) was used in place of HCO-60/LA.

From the above results, it was revealed that although when a compound having an epithelial permeability-enhancing action other than HCO-60/LA was used in the pharmaceutical composition of the present invention, the physiologically active substance could still be delivered to the liver tissues, and specific ones such as a long-chain unsaturated fatty acid and a medium-chain fatty acid that are prepared in the form of a colloidal dispersion system are particularly effective.

Example 10

Study of the Side Effects of VE-siRNA

In order to examine the side effects of VE-siRNA in mice, the following blood test was performed.

HCO-60/LA/VE-siRNA was rectally administered to mice three times with 2-hour intervals. The method of administration was performed in accordance with the method described in Example 3. Three hours after the last administration, the mouse serum was obtained, in which the IFN-α level was measured. Also, in the serum obtained from the mice 24 hours after the last administration, the Cre, ALT, Na, and K levels were each measured. The measurement values were compared between the mouse administered with HCO-60/LA/VE-siRNA and the mouse administered only with PBS. The results thus obtained are shown in Table 1.

|  | IFN-α (pg/ml) | Cre (mg/dl) | ALT (U/l) | Na (mEq/l) | K (mEq/l) |
|---|---|---|---|---|---|
| PBS alone | <12.5 | 0.12 ± 0.01 | 26.0 ± 3.21 | 154 ± 1.2 | 4.93 ± 0.12 |
| Toc-siRNA/MM | <12.5 | 0.13 ± 0.03 | 15.3 ± 1.78 | 150 ± 2.3 | 4.47 ± 0.58 |

As understood from the results of Table 1, in comparison with the mouse administered only with PBS, there was no significant difference in each value in the group of mice administered with HCO-60/LA/VE-siRNA. These results showed that administration of VE-siRNA caused no side effect in vivo.

Example 11

Study of the Delivery of Fluorescently-Labeled VE-siRNA to Each Tissue

In order to confirm if VE-siRNA was delivered specifically to the liver cells, a study of the delivery to organs other than the liver cells was performed as follows.

The pharmaceutical preparation E (HCO-60/LA/VE-siRNA) (pharmaceutical preparation of Example 2) was rectally administered to mice once. The method of administration was performed in accordance with the method described in Example 3. Four hours after the last administration, the lungs, kidneys, spleen, heart, skeletal muscle, and brain were excised from the mice. The method of excision of each organ was performed in accordance with the method described in Example 2. Further, by a similar method to that described in Example 2, a study of the delivery to each tissue was performed. However, clear Cy3 signals were not observed in any tissue of the lungs, kidneys, spleen, heart, skeletal muscle, and brain. From the above results and the results of the delivery to the liver demonstrated above, it was suggested that fluorescence (Cy3)-labeled VE-siRNA was mainly delivered to the liver.

Example 12

Administration of VE-siRNA in the Form of a Hollow-Type Suppository

As the rectal dosage form of VE-siRNA, preparation of a suppository (solid preparation or semi-solid preparation) was attempted, instead of an enema agent (liquid preparation). Firstly, a hollow-type suppository, which can be filled with a liquid or solid preparation, was used for evaluation.
(1) Preparation of Hollow-Type Suppositories The hollow-type suppositories were prepared by the method including the following procedure. That is, 10 g of an oleaginous suppository base (SUPPOCIRE AM PASTILLES, the product of GATTEFOSSE) was melted by heating, to which 1 to 10 g of soybean oil was added. The resulting mixture was mixed to prepare a suppository base. It should be noted that the melting point of the base to which 10 g of soybean oil was added was about 32° C. The suppository base was then melted at about 50° C. and poured into a suppository mold that had been cooled to −20° C. in advance, and at the point at which the part of the base that was in contact with the mold was solidified, the still-unsolidified base around the central axis was removed.
(2) Preparation of Hollow-Type Suppositories Comprising Cy3-Labeled VE-siRNA The pharmaceutical preparation E (HCO-60/LA/VE-siRNA) produced in Example 2 was prepared so that the final concentration of LA was 100 mM, to which taurine (final concentration of 100 mM) was added as a mucous membrane-protecting agent. The resulting mixture was subjected to sonication for a short time while cooling, whereby a mixed micelle solution was prepared. The Cy3-labeled VE-siRNA (1 mg) that was freeze-dried after annealing was dissolved in this mixed micelle solution, and then injected into the hollow-type suppositories produced in the aforementioned Example 12 (1). The resulting suppositories were sealed with the suppository base, whereby hollow-type suppositories comprising Cy3-labeled VE-siRNA were prepared. Also, an enema agent obtained by adding PBS to the mixed micelle solution of Cy3-labeled VE-siRNA (1 mg) to a total volume of 200 μL was used as a positive control pharmaceutical preparation.
(3) In Vivo Evaluation of the Delivery to the Liver Rats (Wistar, male, 7-week-old, body weight of 180 g) were fasted overnight and given 1.2 mL of concentrated milk (milk fat content of 20%) three times with 30-minute intervals from two hours before the drug administration. Thirty minutes after the last milk administration, the rats were anesthetized with Nembutal and the pharmaceutical preparations were each administered through the anus, followed by ligation of the anus. Four hours after administration, the liver and large intestine were excised in accordance with the method described in Example 2 and the distribution of siRNA was observed under a confocal microscope. The results of the observation of the liver tissues are shown in FIG. 11. FIG. 11 a shows the results of the administration of the enema agent, FIG. 11 b shows the results of the administration of the hollow-type suppository, and FIG. 11 c shows the enlarged image of the boxed area in FIG. 11 b. Also, the panels a to c shown in FIG. 11 are each divided in quarters, in which the upper left quarter indicates the results of detection of blue fluorescence of TO-PRO (registered trademark)-3, the upper right quarter indicates the results of detection of green fluorescence of FITC-phalloidin, the lower left quarter indicates the results of red fluorescence of Cy3, and the lower right quarter indicates the results of the superimposition of the results of detection of fluorescence in the upper left quarter, upper right quarter, and lower left quarter.

As shown in FIG. 11, clear fluorescence based on Cy3 was detected both with the administration of the enema agent (FIG. 11 a) and with the administration of the hollow-type suppository (FIGS. 11 b and c), verifying the migration of VE-siRNA to the liver and the distribution of VE-siRNA in the liver.

Example 13

Administration of VE-siRNA in the Form of Suppositories Prepared with Porous Particles Hollow-type suppositories involve a somewhat complex production process. Also, when the hollow-type suppository is internally filled with a liquid preparation, there are problems of dilution and enzymatic degradation in the intestinal lumen after the suppository is administered and the liquid preparation is released into the intestine, as is observed with the enema agent. Meanwhile, as a method for preparation of ordinary suppositories, which are hollow-type suppositories internally filled with a solid preparation, a method of homogeneously adding a freeze-dried solution of a mixed micelle of VE-siRNA to a suppository base may be possible. However, quality control of a freeze-dried preparation of a solution of a mixed micelle of VE-siRNA has many problems. In light of the above, the present inventors conceived of a method of preparation of a suppository, comprising solidifying a solution of a mixed micelle of VE-siRNA into powder in a simple manner by using porous particles having numerous hollow spaces and homogeneously mixing and dispersing the resulting powder in an ordinarily used oleaginous suppository base. The pharmaceutical preparation thus obtained is advantageous in that the production process is simple and VE-siRNA held in the porous particle is protected against enzymatic degradation and dilution in the intestinal lumen.

(1) Preparation of Porous Microspheres (p-MS)

Two grams of ethylcellulose (the product of Nihon Kasei Co., Ltd., STD 7 cps) was dissolved in 16 g of acetone (solution A). Also, 7 g of glycerin and 1 g of an aqueous solution of 5% polyvinyl alcohol (the product of Kuraray Co., Ltd., Kuraray Poval 220C) were mixed (solution B). The solution B was emulsified with the solution A by processing in an emulsifier (Physcotron (registered trademark), the product of Microtec Co., Ltd.) for one minute (oil phase). Meanwhile, 45 g of glycerin and 5 g of an aqueous solution of 5% polyvinyl alcohol (the product of Kuraray Co., Ltd., Kuraray Poval 220C) were mixed to prepare a solution. While stirring the resulting solution at 600 rpm by a Three-One Motor, the oil phase was injected, followed by stirring for one minute. The emulsion thus obtained was immediately poured into 500 mL of purified water, followed by stirring, whereby the oil phase was solidified. Then, the resulting mixture was filtered through a sieve with an opening of 20 μm under reduced pressure to obtain p-MS. The p-MS thus obtained by filtration was washed twice with 100 mL of purified water and re-suspended in a small amount of purified water, and then freeze-dried. The results of scanning electron microscopic observation of the porous microspheres thus obtained are shown in FIG. 12.

(2) Preparation of p-MS Suppositories Comprising Cy3-Labeled VE-siRNA

The p-MS (9 mg) was impregnated with 40 μL of a mixed micelle of Cy3-labeled VE-siRNA (10 mg/mL)/50 mM LA/HCO-60 and homogeneously mixed and dispersed in 500 μL of a mixed base comprising JAPOCIRE (registered trademark) NA 15 PASTILLES:soybean oil at 9:1, whereby p-MS suppositories comprising Cy3-labeled VE-siRNA were produced (FIG. 13). Also, as a control pharmaceutical preparation, a solution obtained by dispersing the aforementioned high-concentration mixed micelle/p-MS comprising Cy3-labeled VE-siRNA in 500 μL of physiological saline was prepared as an enema agent. It should be noted that the aforementioned "JAPOCIRE(registered trademark) NA PASTILLES" is one kind of the suppository bases manufactured by Gattefosse, and specifically refers to a semi-synthetic triglyceride base made of saturated fatty acid having 12 to 18 carbon atoms (hydroxyl value of 10; melting point at 34.5±1.0). In Japan, this product can be purchased by, for example, CBC Co., Ltd.

(3) In Vivo Evaluation of the Migration from the p-MS Pharmaceutical Preparation to the Liver In accordance with Example 12, rats (Wistar, male, 4-week-old, body weight of 80 g) were fasted overnight and then given 0.5 ml of concentrated milk (milk fat content of 20%) three times with 30-minute intervals. Thirty minutes after the last milk administration, the rats were anesthetized with Nembutal and the intestinal tract was washed. Then, the pharmaceutical preparations were each administered through the anus, followed by ligation of the anus. The rats were then held in a Bollman cage. Six hours after administration, the liver, large intestine, kidneys, heart, muscle, and small intestine were excised in accordance with the method described in Example 2 and the distribution of siRNA after administration of each pharmaceutical preparation was observed under a confocal microscope. FIG. 14 shows the images of liver tissues after administration of a control p-MS enema agent (FIG. 14 a) or a p-MS suppository preparation (FIG. 14 b). Also, panels shown in FIGS. 14 a and b are each divided in quarters, in which the upper left quarter indicates the results of detection of blue fluorescence of TO-PRO (registered trademark)-3, the upper right quarter indicates the results of detection of green fluorescence of FITC-phalloidin, the lower left quarter indicates the results of detection of red fluorescence of Cy3, and the lower right quarter indicates the results of the superimposition of the results of detection of fluorescence in the upper left quarter, upper right quarter, and lower left quarter.

In both FIGS. 14 a and b, migration of VE-siRNA based on the fluorescence of Cy3 was observed in some areas. Particularly, although the fluorescence intensity itself is low, fluorescence of Cy3 was detected in many liver cells as a result of administration of the p-MS suppository preparation.

Similarly, FIG. 15 shows the results of examination of the distribution of Cy3-VE-siRNA in the large intestine tissues six hours after administration. FIGS. 15 a and b show the results of observation of the mucosal tissues of the upper part of the large intestine and FIGS. 15 c and d show the results of observation of the mucosal tissues of the lower part of the large intestine. Also, FIGS. 15 a and c show the results of the administration of the p-MS enema agent and FIGS. 15 b and d show the results of the administration of the p-MS suppository.

In comparison with the lower part of the large intestine (FIG. 15 d), migration of Cy3 to and residual Cy3 in the mucosal tissues of the upper part of the large intestine were more intensely observed (FIG. 15 b) as a result of the administration of the p-MS suppository. Meanwhile, when the p-MS enema agent was administered, migration of Cy3 to and residual Cy3 in the lower part of the large intestine (FIG. 15 c) were the same level as that observed with the administration of the suppository, whereas migration of Cy3 to and residual Cy3 in the upper part of the large intestine were almost not observed (FIG. 15 a). Also, Cy3 was almost not detected in the small intestine, muscle, heart, and kidneys after administration of the p-MS enema agent and the p-MS suppository. These results suggested that Cy3-labeled VE-siRNA was more efficiently delivered to the liver cells than to the large intestinal part by preparing it as a p-MS suppository.

As shown above, it was suggested that VE-siRNA could possibly be prepared not only as an enema agent, but also as a suppository by using a hollow-type suppository. It was further shown that it was possible to easily homogeneously disperse a liquid agent in an oleaginous suppository base and prepare a suppository by using porous particles, enabling more efficient delivery of VE-siRNA to the liver tissues.

Example 14

Inhibitory Effect of the Transthyretin Gene-Targeted VE-siRNA on the Expression of the Gene A study was attempted using siRNA targeting the transthyretin (TTR) gene as the physiologically active substance of the present invention other than siRNA targeting the mouse apoB gene. As the aforementioned siRNA, siRNA consisting of a sense strand (27 mer) consisting of SEQ ID NO: 3 (5'-GUAACCAAGAGUAUUCCAUUUUUACUA-3') and an antisense strand (29 mer) consisting of SEQ ID No: 4 (5'-UAGUAAAAAUGGAAUACUCUUGGUUA-CAC-3') was synthesized and used.

(1) Synthesis of VE-siRNA

To the 5' end of the antisense strand of the aforementioned siRNA targeting the TTR gene, α-tocopherol (Toc), which is one of the naturally occurring isomers of vitamin E, was covalently bound as an introduction substance into lipoprotein by a phosphate bond, whereby VE-siRNA was prepared.

(2) Preparation of VE-siRNA-Comprising Enema Agents

An enema agent (HCO-60/LA/VE-siRNA) was prepared in accordance with the method described in the aforementioned Example 2 (1) except for using the VE-siRNA obtained in the aforementioned Example 14 (1) in place of the VE-siRNA used in the aforementioned Example 2 (1). Also, as a control, a control enema agent (HCO-60/LA/PBS) was prepared by mixing a mixed micelle solution with PBS in place of VE-siRNA.

(3) In Vivo Evaluation of the Delivery to the Liver

The hTTR V30M Tg mice (female, 6-month-old, body weight of 30 g, five mice in one group), which are transgenic mice having the human transthyretin (hTTR) gene, were anesthetized with Nembutal and the feces remaining near the anus were excreted by mild massage on the lower abdomen, after which the enema agents prepared in the aforementioned (2) were each administered through the anus (dose per administration: 10 mg/kg). After administration, the mice were left for 20 minutes with the anus clipped. The mice were then unclipped and returned to a normal rearing cage. The aforementioned administration method was performed three times a day, every four hours, for five consecutive days. Also, the blood was drawn before administration and six, nine, and 12 days after initiation of the administration, and the whole blood was centrifuged to obtain the serum. Subsequently, the concentration of hTTR (mg/dL) in each serum fraction was measured. The concentrations of hTTR (mg/dL) in the serum before administration and the serum on the $12^{th}$ day after initiation of the administration are shown in FIG. 16. As understood from FIG. 16, it was verified that TTR secretory proteins in the serum could be suppressed by administration of an enema agent consisting of TTR-targeted VE-siRNA and the above mixed micelle.

INDUSTRIAL APPLICABILITY

The present invention can be favorably used in the field associated with disease treatment, in more detail, a field associated with a pharmaceutical composition for transcolonic absorption.

---

The invention claimed is:

1. A method for delivering a nucleic acid drug to the liver of a vertebrate, the method comprising:
   inducing the formation of endogenous lipoprotein particles in the vertebrate; and
   administering a pharmaceutical composition to the large intestine of the vertebrate, wherein the pharmaceutical composition comprises:
   (a) the nucleic acid drug covalently bound to Vitamin E, and
   (b) a composition that enhances epithelial permeability of the nucleic acid drug through the mucosal epithelium of the large intestine, comprising polyoxyethylene hydrogenated castor oil and at least one compound selected from linoleic acid, oleic acid, linolenic acid, docosahexaenoic acid, and eicosapentaenoic acid; and
   wherein the nucleic acid drug is specifically delivered to the liver and the nucleic acid drug exerts a physiologically active effect at least in the liver.

2. The method according to claim 1, wherein the nucleic acid drug covalently bound to Vitamin E has a molecular weight in the range of 5000 to 50000 Da.

3. The method according to claim 1, wherein the nucleic acid drug is selected from siRNA, shRNA, an antisense oligonucleotide, an antagomir, a nucleic acid aptamer, a ribozyme, and a decoy.

4. The method according to claim 1, wherein the nucleic acid drug suppresses the expression of a gene targeted by said nucleic acid drug.

5. The method according to claim 1, wherein the composition that enhances epithelial permeability of the physiologically active substance comprises one of the following (i) to (iv):
   (i) polyoxyethylene hydrogenated castor oil and linoleic acid;
   (ii) polyoxyethylene hydrogenated castor oil and docosahexaenoic acid;
   (iii) polyoxyethylene hydrogenated castor oil and eicosapentaenoic acid; or
   (iv) polyoxyethylene hydrogenated castor oil and oleic acid.

6. The method according to claim 5, wherein the nucleic acid drug is selected from si RNA, shRNA, an antisense oligonucleotide, an antagomir, a nucleic acid aptamer, a ribozyme, and a decoy.

7. The method according to claim 1, wherein the pharmaceutical composition is administered in the dosage form of a suppository or an enema agent.

8. A method for suppressing the expression of a gene within the liver of a vertebrate, comprising:
   inducing the formation of endogenous lipoprotein particles in the vertebrate; and
   administering a pharmaceutical composition to large intestine of the vertebrate in a dosage form for transcolonic absorption,
   wherein the pharmaceutical composition comprises:
   (a) a nucleic acid drug that suppresses expression of a gene and is selected from siRNA, shRNA, an antisense oligonucleotide, an antagomir, a nucleic acid aptamer, a ribozyme, and a decoy, wherein said nucleic acid drug is covalently bound to Vitamin E; and
   (b) a composition that enhances epithelial permeability of the nucleic acid drug through the mucosal epithelium of the large intestine, comprising polyoxyethylene hydrogenated castor oil and at least one compound selected from linoleic acid, oleic acid, linolenic acid, docosahexaenoic acid, and eicosapentaenoic acid; and
   wherein the nucleic acid drug is specifically delivered to liver cells.

* * * * *